United States Patent [19]
Uchida et al.

[11] Patent Number: 5,772,962
[45] Date of Patent: Jun. 30, 1998

[54] ANALYZING APPARATUS USING DISPOSABLE REACTION VESSELS

[75] Inventors: Hiroyasu Uchida; Takashi Sato; Kenichi Itoh, all of Hitachinaka, Japan

[73] Assignee: Hitachi, Ltd., Tokyo, Japan

[21] Appl. No.: 654,714

[22] Filed: May 28, 1996

[30] Foreign Application Priority Data

May 29, 1995 [JP] Japan ................................. 7-130733

[51] Int. Cl.⁶ .................................................. G01N 35/10
[52] U.S. Cl. ............................ 422/67; 422/63; 422/64; 422/65; 422/100; 436/43; 436/47; 436/48; 436/50
[58] Field of Search ................................. 422/63, 64, 65, 422/67, 100, 104; 436/43, 47, 48, 49, 50, 54, 174, 180

[56] References Cited

U.S. PATENT DOCUMENTS

| | | | |
|---|---|---|---|
| 4,058,367 | 11/1977 | Gilford | 422/65 |
| 4,731,225 | 3/1988 | Wakatake | 422/65 |
| 4,785,677 | 11/1988 | Higo | 73/864.14 |
| 5,055,408 | 10/1991 | Higo et al. | 436/48 |
| 5,122,342 | 6/1992 | McCulloch et al. | 422/65 |
| 5,158,895 | 10/1992 | Ashihara et al. | 436/526 |
| 5,260,872 | 11/1993 | Copeland et al. | 364/413.07 |
| 5,384,093 | 1/1995 | Ootani et al. | 422/63 |
| 5,443,791 | 8/1995 | Cathcart et al. | 422/65 |
| 5,455,006 | 10/1995 | Aota et al. | 422/63 |
| 5,472,669 | 12/1995 | Miki et al. | 422/63 |
| 5,578,269 | 11/1996 | Yaremko et al. | 422/64 |
| 5,582,796 | 12/1996 | Carey et al. | 422/65 |

FOREIGN PATENT DOCUMENTS

| | | |
|---|---|---|
| 0410645 | 1/1991 | European Pat. Off. . |
| 62-44222 | 9/1987 | Japan . |
| 4-145370 | 5/1992 | Japan . |
| 92/05448 | 4/1991 | WIPO . |

OTHER PUBLICATIONS

Medicine and Pharmaceutics, vol. 28, No. 6, Dec., 1992, pp. 1259–1264.
Equipment/Reagent Seminar of 24th General Meeting of Japan Society for Clinical Laboratory Automation, 1992.
Clinical Chemistry, vol. 40, No. 3, 1994, "Evaluation of Ciba Corning ACS:180 Automated Immunoassay System", Mora–Brugues et al, pp. 407–410.

*Primary Examiner*—Long V. Le
*Attorney, Agent, or Firm*—Fay, Sharpe, Beall, Fagan, Minnich & McKee

[57] ABSTRACT

Unused reaction vessels and unused nozzle tips are arranged in a matrix on a vessel magazine and a tip magazine, respectively. A carrying mechanism for moving a gripping mechanism along X- and Y-axes seizes unused nozzle tips on the tip magazine one by one in order, and transfers them to a tip attaching station. The carrying mechanism also seizes unused reaction vessels on the vessel magazine one by one in order starting from one end of the first row. A delivery mechanism, after having attached a nozzle tip on the tip attaching station to a nozzle holder, pours sample and reagent into a reaction vessel on a delivery station. The reaction vessel is carried by a gripping mechanism to an incubator where the mixture of sample and reagent is incubated. After incubation, the reaction vessel is transferred to a shipper station where the reaction solution is extracted by suction with a shipper nozzle which introduces the solution into the flow cell of a measuring device. Prior to the above analyzing operation, the gripping mechanism with its fingers kept closed moves about over the delivery station and the incubator to checking for any obstacles, and disposes of any as necessary.

15 Claims, 11 Drawing Sheets

ANALYZING APPARATUS USING DISPOSABLE REACTION VESSELS

BACKGROUND OF THE INVENTION

The present invention relates to an analyzing apparatus, and particularly to an analyzing apparatus suitable for highly sensitive measurement as in immunoassay.

Immunoassay used for laboratory tests includes enzyme-linked immunoassay using enzymes as a marker, fluorescent immunoassay using fluorescent dyes, etc., and has been widely used in laboratory tests. Recently, a more sensitive immunoassay using a luminescent material as a marker has been developed and is being put to use for determination of various hormones or for detection of infectious diseases (such as hepatitis and AIDS).

When immunoassay is applied for determination of a trace amount of substance in body fluid, it is extremely important to avoid cross-contamination between test samples. Some apparatuses incorporating devices to avoid cross-contamination have been presented where parts or components that come into direct contact with samples or reagents are used only once and disposed of after measurement.

Such apparatuses include (1) a full-automatic luminescent immunoassay as described in "Medicine and Pharmaceutics", 28(6): 1259–1264 (December, 1992), (2) a high speed, full automatic luminescent immunoassay as presented in Equipment/Reagent Seminar of "24th General Meeting of Japan Society for Clinical Laboratory Automation" (1992), and (3) an automated immunoassay system as introduced in "Clinical Chemistry" 40(3): 407–410 (1994).

With these first and second apparatuses of the prior art, a disposable tip is attached to the end of a nozzle used for extracting samples, and the tip thus prepared is used for collecting samples. Further, reagents have been placed in disposable cartridges prior to use. Measurement consists of a series of the following steps: The reagent cartridge is transferred to the reaction line maintained at a specified temperature; a sample is added to the reaction line; the mixture is stirred; B/F (Bind/Free) separation is performed; a labeled antibody is copied; second B/F separation is made; a luminescent substance is added; and finally the light intensity of luminescence is measured.

A third apparatus of prior art has a constitution such that a disposable tip is attached to the end of a nozzle to be used for collecting a sample, reagent has been stored in a bottle of a big capacity, and a necessary amount of reagent is taken from the bottle and transferred to a disposable reaction vessel when in use. Measurement consists of a series of the following steps: a reagent is transferred to the reaction line; a sample is added to the reaction line; the mixture is stirred; B/F (bound/free components) separation is performed; a labeled antibody is added; a second B/F is made; a luminescent substance is added; and finally the light intensity of the luminescence is measured.

There are also analyzers based on the prior art and used not for luminescent immunoassay but for general analysis or for pretreatment in analysis, which have a constitution such that, instead of the reaction line, a single robot arm is installed which can turn round or move up and down, and has reagents or reaction vessels arranged around it when used for analysis or for pretreatment, as described in Japanese Patent Laid-Open No. 4-145370 and Japanese Patent Publication No. 62-44222.

The above-described first, second and third systems employ disposable nozzle tips, disposable reagent cartridges, or disposable reaction vessels so as to avoid cross-contamination. They have, however, a problem that they must be made into large-sized machines because a series of steps should proceed on the reaction line.

The systems as described in Japanese Patent Laid-Open No. 4-145370 and Japanese Patent Publication No. 62-44222 have a constitution such that a robot arm which can turn round and move up and down is placed at the center, and thus they have also a problem that they must be made into large-sized machines.

SUMMARY OF THE INVENTION

An object of the present invention is to provide an analyzing apparatus small in overall size, by narrowing the range across which reaction vessels must be carried.

Another object of the present invention is to provide an analyzing apparatus which allows the operator to avoid direct contact with reaction vessels containing samples as much as possible.

The present invention applies to an analyzing apparatus wherein a sample(s) and a reagent(s) are allowed to react in a reaction vessel, the reaction solution is introduced into a measuring device, and after use the reaction vessel is disposed of.

The analyzing apparatus according to the present invention is provided with a gripping means capable of holding reaction vessels, a carrying means for carrying the gripping means along X- and Y-axes, a delivering means for delivering samples and reagents to reaction vessels placed on a delivery station, an incubator for incubating the mixture of sample and reagent in the reaction vessel, and a vessel magazine incorporating a plurality of unused reaction vessels, and has a constitution such that the delivery station, the incubator and the vessel magazine are placed within the movable range of the gripping means.

A preferred embodiment of the present invention is provided with a control means for controlling the operation of the carrying means so as to check for presence of an obstacle by moving the gripping means over the delivery station and the incubator, before the gripping means starts to carry unused reaction vessels on the vessel magazine to the delivery station.

The carrying means has a moving member incorporating said gripping means, and the moving member has a detecting means for detecting presence of an obstacle. When the gripping means is engaged in detection of the presence of obstacles, it lowers its arm on the delivery station and the incubator with its finger members kept closed. When the gripping means detects an obstacle during inspection, the control means makes the gripping means grip the obstacle and carry it to a waste position.

The vessel magazine has rows of unused reaction vessels. The control means controls said carrying means such that the latter carries one reaction vessel after another in order from one end of the first row to the delivery station. The carrying means has a detecting means capable of detecting the presence of reaction vessels, and when the detecting means detects a reaction vessel at one end of the first row of the vessel magazine, the control means resets a sequence according to which reaction vessels should be carried.

The gripping means has a pair of finger members different in size, and when the gripping means grips a reaction vessel, the fingers are so positioned against that vessel that one finger is placed between the vessel and an adjacent vessel, the other between the vessel and a blank space. The carrying means has another detecting means for detecting whether the gripping means are kept closed or opened.

A tip magazine has rows of unused nozzle tips arranged in an orderly fashion. An unused nozzle tip is attached to the delivering means on a tip attaching station. The external diameter of the head of a reaction vessel is substantially the same as the external diameter of the head of a nozzle tip. The gripping means grips reaction vessels and nozzle tips by the head.

A plurality of reaction vessels are placed on the delivery station. The delivering means, after having introduced a sample(s) and a diluted solution(s) into the first reaction vessel on the delivery station, transfers by pipetting a portion of the diluted sample in the first reaction vessel to the second one on the delivery station.

DESCRIPTION OF THE PREFERRED EMBODIMENT

Figure 1:
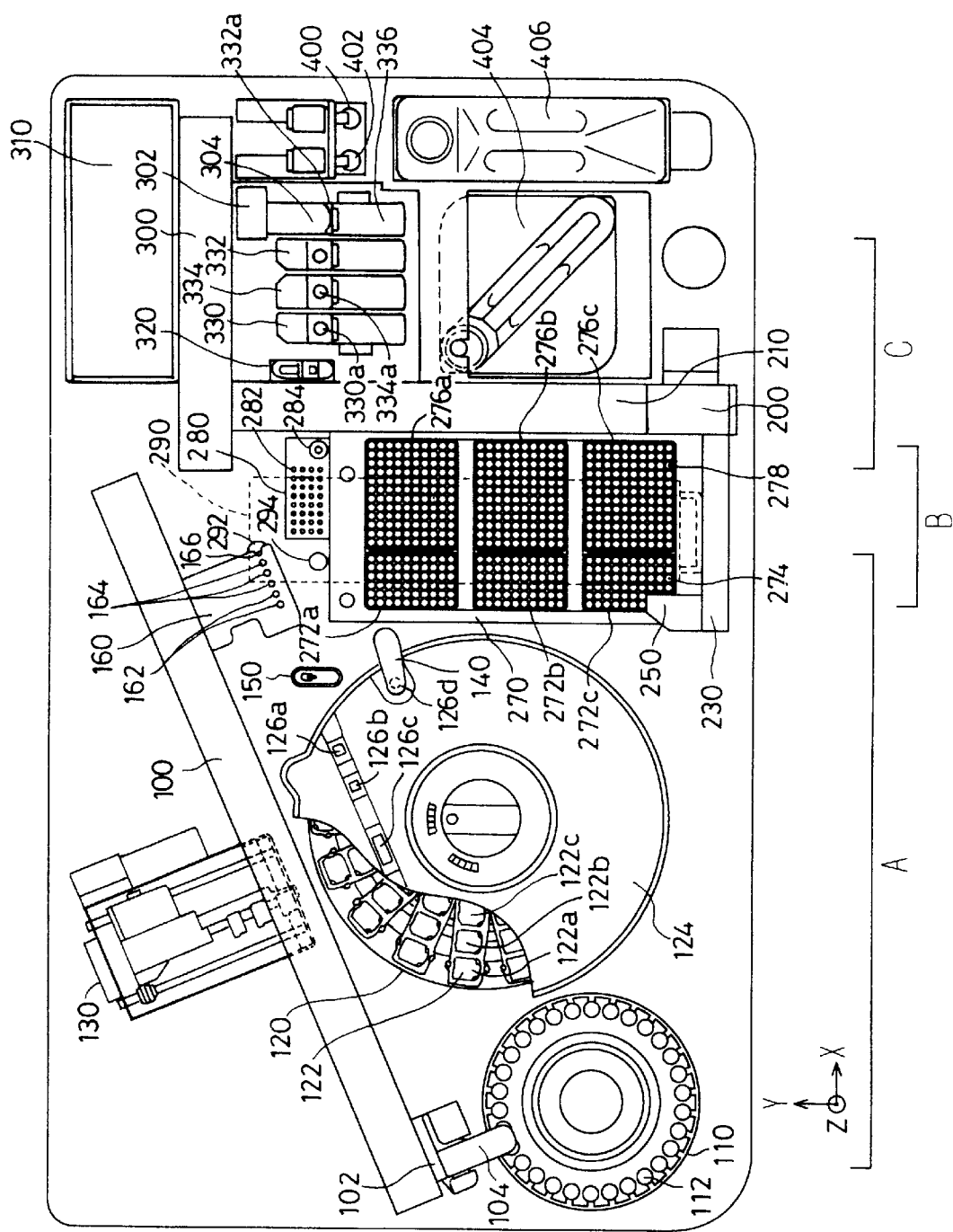
FIG. 1 gives a top view of an immunoassay analyzer embodying of the present invention.

An embodiment of the present invention will be described below with referring to the drawings.

FIG. 1 gives a top view of an analyzer for luminescent immunoassay prepared as one example of this invention.

This embodiment is provided with three driving mechanisms: a delivering mechanism 100, a carrying mechanism 200 and a shipper mechanism 300. The delivering mechanism covers section A, the carrying mechanism section B, and the shipper mechanism section C. Sections A and B are overlapped partly, and at the overlapped part the delivering mechanism and the carrying mechanism join together. Further, sections B and C are overlapped partly, and at the overlapped part the carrying mechanism and the shipper mechanism join together. The delivering mechanism can move along the Z-axis or the axis vertical to the drawing in FIG. 1, and move along two axes normal to the Z-axis. The carrying mechanism 200 can move along three axes, that is, along the Z-axis or the axis vertical to the drawing in FIG. 1, and the X- and Y-axes normal to the Z-axis. The shipper mechanism 3 can move along two axes, that is, the Z-axis vertical to the drawing in FIG. 1 and an axis normal to the Z-axis.

To the delivering mechanism 100, a nozzle carrier 102 is mounted, which can move obliquely crosswise in FIG. 1. The nozzle carrier moves on a rail of the delivering mechanism 100. On the nozzle carrier 102 is placed a nozzle holder 104 which can move along the Z-axis or the axis vertical to the drawing in FIG. 1. Because the nozzle holder 104 can move up and down, and the nozzle carrier 102 with the nozzle holder 104 placed thereupon can move obliquely crosswise, the delivering mechanism 100 can move along two axes.

At the left end of section A within which the delivering mechanism 100 moves about, a sample carrying mechanism 110 is placed. On the sample carrying mechanism 110, thirty sample vessels 112 are placed in a circle. The sample vessels can be freely removed from the sample carrying mechanism 110. Thirty sample vessels 112 have been placed on a donut-shaped disc, and then the assembly is placed on the sample carrying mechanism 110. When quick measurement is needed, however, it is possible to place sample vessels 112 one by one on the sample carrying mechanism 110 to be ready for measurement. In each sample vessel 112 a sample to be tested is placed. The sample carrying mechanism 110 is driven by a pulse-motor which is not shown in the figure, such that a sample vessel 112 is placed beneath the nozzle holder 104, and the sample in the sample vessel 112 is extracted by suction into the nozzle holder 104.

In section A within which the delivering mechanism 100 moves about, adjacent to the sample carrying mechanism 110 is placed a reagent carrying mechanism 120. On the reagent carrying mechanism 120 are placed units 122 of three reagent vessels 122a, 122b and 122c. On the sample carrying mechanism 120, 18 units of reagent vessels 122 can be placed. Eighteen units of reagent vessels can contain, in addition to units of reagent for analysis, units of diluting solution, units of calibrator, or units of spare reagent in case the reagent in the reagent units has been consumed in analysis and remaining amounts are insufficient for subsequent analysis. Accordingly, normally this analyzer allows 18 different assays at maximum, but if a unit of reagent is used in combination with other units of different reagents, far more assays can be performed. A reagent unit comprises a first reagent, a second reagent and beads: a bead-containing solution is placed into the reagent vessel 122a, a first reagent into the vessel 122b and a second reagent into the vessel 122c. The beads are magnetic beads of 2 $\mu$m size and coated with appropriate antibodies, and act as a support for immunological reaction. When only the first reagent is used depending on the nature of assay, the reagent vessel 122b is spared from use.

The reaction vessels 122a, 122b and 122c are covered with caps, and the top of the reagent carrying mechanism 120 is closed with a lid 124. The chamber within the reagent carrying mechanism 120 is kept under thermostatic control. Accordingly, the top of the chamber is closed with the lid 124, thereby separating the chamber from atmosphere. A reagent unit 122 placed in the reagent carrying mechanism 120 has bar-code labels attached on the side of individual vessels which indicate the kind of assay those vessels are undergoing. A cap operating mechanism 130 reads the bar-codes, checks whether the vessels of interest are required for assay now in progress, and, when they are right, opens/closes any one or all of the reagent vessels 122a, 122b and 122c as appropriate.

On the lid 124 are prepared openings 126a, 126b and 126c along the course the nozzle holder 104 takes during operation. The opening 126a is prepared just above the reaction vessel 122a, the opening 126b above the vessel 122b, and the opening 126c above the vessel 122c.

The reagent carrying mechanism 120 is turned round with a pulse motor not illustrated in the figure, and is properly positioned with respect to the cap operating mechanism 130, and any one or all of required reaction vessels 122a, 122b and 122c are opened/closed. In addition, beneath either one of the openings 126a, 126b or 126c, is positioned an appropriate one of the reaction vessels 122a, 122b and 122c. The reagent or the bead-containing solution in vessels 122a, 122b and 122c as appropriate is extracted by suction into the nozzle holder 104.

It is possible to insert a stirring mechanism 140 through another opening on the lid 124 of the reagent carrying mechanism 120 into the reaction vessel 122a, and to stir the bead-containing solution therein. This maneuver allows beads of magnetic particles to disperse evenly in the solution. The stirring mechanism 140 can be pivoted towards a washing basin 150, and it can be washed with cleaning water in the washing basin 150.

In section A within which the delivering mechanism 100 moves about, and on the right of the right end of the reagent carrying mechanism 120 is placed a buffer plate 160. To the buffer plate 160 are mounted two relay stations 162 acting as stations for tip attachment, and three delivery stations 164. The relay stations 162 and the delivery stations 164 are all circular openings formed on the buffer plate 160, and arranged beneath the course the nozzle holder 104 of the delivering mechanism 100 takes during operation. To each relay station 162 is fitted a disposable nozzle tip, which is then attached to the end of the nozzle holder 104 to serve for delivery of samples or reagents. To each delivery station 164 is fitted a disposable reaction vessel, into which the sample or reagent that has been introduced by suction into the nozzle holder 104 is ejected. The details of the relay station 162 and the delivery station 164 will be given later.

The buffer plate 160 is made so high as to allow the upper end of a nozzle tip or a reaction vessel placed thereupon to be flush with the lid 124 covering the reagent carrying mechanism 120, and the level the nozzle holder 104 takes when elevated at maximum is set to the same height. The level of the tip of a nozzle tip, when it is held by the nozzle holder 104, is slightly above the buffer plate 160 and the lid 124.

The washing basin 150 is placed between the reagent carrying mechanism 120 and the buffer plate 160. The washing basin has a nozzle through which cleaning water is discharged. When the delivering mechanism 100 is positioned just above the washing basin 150, cleaning water is expelled from the tip of the nozzle, thereby washing out residue of samples or reagents adhered to the outer surface around the nozzle tip attached to the end of the nozzle holder 104.

As is obvious from the above explanation, the nozzle holder 104 on the delivering mechanism 100 moves along a line above the sample carrying mechanism 110, the reagent carrying mechanism 120, the washing basin 150 and the buffer plate 160, and, when it is positioned just above the sample carrying mechanism 110, the reagent carrying mechanism 120, or the buffer plate 160, it can move up and down along the Z-axis, while being able to move along two axes.

The carrying mechanism 200 as illustrated in FIG. 1 is provided with a Y-axis frame 210 placed crosswise along Y-axis, and an X-axis frame 230 placed lengthwise along X-axis which is normal to the Y-axis frame 210 and movable with respect to the fixed Y-axis frame 210. The X-axis frame 230 can move along the Y-axis. To the X-frame 230 is mounted an X-carriage 250 capable of moving along the X-axis. Further, the X-carriage 250 incorporates a pair of fingers capable of moving along the Z-axis. In short, the carrying mechanism 200 can move along three axes. The X-carriage 250 acts as a moving member incorporating a gripping mechanism 251.

In section B within which the carrying mechanism 200 moves about, is placed a stocker 270. At the left in the stocker 270 are arranged three vessel magazines 272a, 272b and 272c. On each of these three vessel magazines 272a, 272b and 272c, are prepared circular openings arranged in a pattern of a matrix comprising 6 columns and 10 rows, and to each opening is fitted a disposable reaction vessel 274. As one vessel magazine can have 60 reaction vessels placed thereupon, the three vessel magazines are to contain 180 reaction vessels in total. The vessel magazines 272a, 272b and 272c can be removed from the stocker 270 independently of each other. Thus, normally replacement of reaction vessels can take place as an assembly contained in a vessel magazine. Of course, it is possible to replace one reaction vessel with another in a given magazine.

Towards the inner side of the stocker 270 are placed, besides the vessel magazines, three tip magazines 276a, 276b and 276c, and each of the tip magazines 276a, 276b and 276c has round openings arranged in a matrix of 12 columns and 10 rows. To each opening is fitted a disposable nozzle tip 278. As one tip magazine can have 120 nozzle tips placed thereupon, the three tip magazines are to contain 360 nozzle tips in total. The tip magazines 276a, 276b and 276c can be removed from the stocker 270 independently of each other. Thus, normally replacement of nozzle tips can take place as an assembly contained in a tip magazine. Of course, it is possible to replace one nozzle tip with another in a given magazine.

In the range within which the carrying mechanism 200 moves about, is placed the buffer plate 160. Namely, the buffer plate 160 is positioned just at the junction between the delivering mechanism 100 and the carrying mechanism 200.

The gripping mechanism mounted to the X-carriage 250 picks up a reaction vessel from the vessel magazine 272a, 272b or 272c in the stocker 270, carries it towards the buffer plate 160, and places it on the round opening on the delivery station 164. Further, the gripping mechanism mounted to the X-carriage 250 picks up a nozzle tip from the tip magazine 276a, 276b or 276c, carries it towards the buffer plate 160, and place it on the round opening on the relay station 162.

On the upper right of section B within which the carrying mechanism 200 moves about, is placed an incubator 280 that is like a block. The interior of the incubator 280 is kept by thermostat at a specific temperature, or for example at 37° C., and on its top surface is mounted a vessel holder 282 which has 32 openings arranged in a matrix composed of 8 rows and 4 columns and each having a similar contour to the reaction vessel 274. Accordingly, when a reaction vessel into which reagent and sample have been introduced is carried by the carrying mechanism 200 to an opening of this vessel holder 282, inserted into it and kept there, the sample and reagent in the reaction vessel can be maintained at the specified temperature.

In the upper right of section B within which the carrying mechanism 200 moves about, and to the right of the vessel holder 282 of the incubator 280 is placed a shipper station 284. A reaction vessel, after having stayed at a specific time in the incubator 280 for reaction, is carried to the position of the shipper station 284 by the carrying mechanism 200. The shipper station 284 is the station at which the shipper mechanism 300 as described later extracts by suction the sample and reagent having reacted for a specified time, and then carries the sample and reagent to a measuring device 310.

In section B within which the carrying mechanism 200 moves about, below the incubator 280, vessel magazines 272a, 272b and 272c, and below tip magazines 276a, 276b and 276c, and in the body of the system itself, is placed a waste box as indicated in the figure with dotted lines. The waste box has two openings; one is an opening for nozzle tips 292 underlying a waste outlet 166 prepared on the buffer plate 160, and the other is an opening 294 for vessels prepared at left of the incubator 280.

A disposable nozzle tip attached to the end of the nozzle holder 104, after having been used for delivery of sample or reagent, is removed from the nozzle holder 104 at a position over the waste outlet 166 prepared on the buffer plate 160. It is transferred, through the underlying opening for nozzle tips 292, to the waste box to be disposed of later. The waste outlet 166 prepared on the buffer plate 160 will be detailed later with reference to FIG. 2.

The reaction vessel, after having allowed sample and reagent to react and the reaction mixture to be removed by suction to the shipper station 284, is carried by the carrying mechanism 200 from the shipper station 284 to a position over the opening for vessels 294, and transferred, through the opening for vessels 294, into the waste box 290 to be disposed of later.

To the waste box 290 is attached a handle as indicated with dotted lines in the figure, and one can remove the waste box 290 from the system from the front, by pulling the handle towards himself.

As is obvious from the detailed explanation above, the X-carriage 250 of the carrying mechanism 200 moves along 2 axes or the X- and Y-axes over the stocker having vessel magazines 272a, 272b and 272c, and tip magazines 276a, 276b and 276c placed thereupon, the buffer plate 160 and the incubator 280. Further, above a reaction vessel 274 and a nozzle tip 278, above the relay station 162 and delivery station 164 on the buffer plate 160, above the vessel holder 282 on the incubator 280, or above the shipper station 284, the gripping mechanism can move up and down; the gripping mechanism can move along three axes at these sites.

To the shipper mechanism 300, a shipper nozzle 304 movable along the X-axis is attached. To a nozzle carrier 302, a shipper nozzle 304 is mounted, which moves up and down along the Z-axis in FIG. 1. Accordingly, as the shipper nozzle 304 moves up and down, and the nozzle carrier 302 incorporating the shipper nozzle 304 moves along the Y-axis, the shipper mechanism 300 can move in two directions normal to each other.

The left margin of section C within which the shipper mechanism 300 moves about is occupied by the shipper station 284 described above. Namely, the shipper station 284 is at the junction between the moving ranges of the carrying mechanism 200 and the shipper mechanism 300.

The shipper nozzle 304 in the shipper mechanism 300 extracts sample and reagent by suction from a reaction vessel placed on the shipper station 284, introduces it into the measuring device 310, and allows it to measure the intensity of light emanating from the sample.

The measuring device 310 incorporates a flow cell interconnected with the shipper nozzle 304, and a light detector placed adjacent to the flow cell.

In section C within which the shipper mechanism 300 moves about, and to the right of the shipper station 284 which is positioned at the left margin of section C, a washing basin 320 for shipper nozzles is placed. It has the same constitution as does the washing basin 150, and washes the outer surface of a shipper nozzle 304 with cleaning water.

In section C within which the shipper mechanism 300 moves about, and to the right of the washing basin for shipper nozzle 320, are arranged a buffer tank 330, a cleaning water tank 334, another buffer tank 332 and another cleaning water tank 336 in this order. Openings 330a, 334a and 332a a made on the buffer tank 330, cleaning water tank 334 and buffer tank 332 respectively, and an opening of the cleaning water tank 336 not illustrated in the figure, are arranged along a line, and on the extension of this line are also arranged the shipper station 284 and the washing basin for shipper nozzle 320. The shipper nozzle 304 moves above this line.

Because a level sensor attached adjacent to the tip of the shipper nozzle 304 allows detection of any residual volume of liquids in the buffer tank 330 and the cleaning water tank 334, it is possible, when the residual volume of the liquid is too small, to switch from one combination of the buffer tank 330 and cleaning water tank 334, to the other combination of the buffer tank 332 and cleaning water tank 336, and vice versa. This level sensor is also used for detecting the level of solution in a reaction vessel.

A syringe pump 400 is connected to the shipper nozzle 304, and allows it to extract by suction solution from reaction vessels on the shipper station 284, buffer from the buffer tanks 330 and 332, and cleaning water from the cleaning water tanks 334 and 336. Another syringe pump 402 is connected to the nozzle holder 104, and allows it to extract by suction sample from sample vessels on the sample carrying mechanism 110, and reagent from the reagent vessels 122a, 122b and 122c on the reagent carrying mechanism 120, and to eject sample and reagent into reaction vessels on the delivery station 164 of the buffer plate 160.

In front of the buffer tanks 330 and in front 332, and in front of the cleaning water tanks 334 and 336, is placed a waste tank 404. Into this waste tank 404 are dumped washing byproducts from the washing basin 150, washing byproducts from the washing basin for shipper nozzles 320, and solution, buffer and washing byproducts discharged from the flow cell in the measuring device 310. To the right of the waste tank 404 is placed a water supply tank 406. Clean water in this tank 406 is distributed to the washing basin 150 and the washing basin for shipper nozzle 320.

Next, operation of the system at large will be outlined below.

To a microcomputer which has been incorporated into the system as a control unit, necessary items for analysis including sample numbers are fed through an input-feeding device such as a keyboard. Here, as an example analyses H, I and J are made for sample 1, and the same analysis is repeated for sample 2.

The analyses H and I are based on two-step reactions: the first step is to mix reagent, beads and sample to react for several minutes; and the second is to add reagent or beads thereto as appropriate to react further for several minutes. The analysis J consists of a one-step reaction: All elements necessary for analysis, that is, reagent, beads and sample, are mixed all at once to react. Then, the reaction process proceeds as follows for these analyses: In analysis H, beads, a first reagent R1 and sample S are allowed to react in the first step, and to this product is added a second reagent R2 in the second step; in analysis I, a first reagent R1 and sample S are allowed to react in the first step, and to this product are added beads and a second reagent R2; in analysis J, beads, a first reagent R1, a second reagent R2 and sample S are added simultaneously.

Example 1 concerns analysis H for sample 1, and its operation will be outlined below.

When analysis starts, the X-carriage 250 or a moving member attached to the carrying mechanism 200 moves from a standby position to the left uppermost position of the tip magazine 276a, and holds an unused nozzle tip on that position. Further, the X-carriage 250 transfers the nozzle tip to the left opening of the relay station 162 on the buffer plate 160.

The X-carriage 250 starts to pick up a nozzle tip from the left uppermost position of the tip magazine 276a, then advances in order towards the right in the same row. This first row has 12 nozzle tips. Thus, after the 12 nozzle tips have been used up, the X-carriage advances to the second row. After the next 12 nozzle tips have been used up, the X-carriage advances to the third row. When 120 nozzle tips have been used up in this manner, the X-carriage moves to the left uppermost position of the next tip magazine 276b. When all the nozzle tips in the tip magazine 276b have been used up, the X-carriage advances to the tip magazine 276c.

The nozzle holder 104 in the delivering mechanism 100 starts to move from a standby position above the washing basin 150 towards the upper right until it reaches a position just above the left opening of the relay station 162 on the buffer plate 160. Then, the nozzle holder 104 descends so low as to make the external circumference of its end to fit to the internal circumference of the nozzle tip placed thereupon, thereby allowing the latter to attach to its end. The nozzle holder 104 with the nozzle tip attached to its end moves towards the lower left until it reaches a position above the opening 126a prepared on the lid 124 of the reagent carrying mechanism 120. The nozzle tip descends until it reaches a reagent vessel 122a placed just below the opening 126a, to draw in by suction the beads containing solution $B_H$ in the vessel 122a which is to be used for analysis H. The volume to be extracted is assumed 50 µl here. However, the volume to be extracted varies depending on the kind of analysis; it may be 20 µl or another. The volume to be extracted can be varied by adjustment of the syringe pump 402.

The microcomputer incorporated in the system, being well conscious of implementation of analysis H, places a unit of reagent vessels 122 containing reagents necessary for analysis H just opposite to the cap operating mechanism 130 before the delivering mechanism 100 enters into action. This placement takes place as a result of reading by the microcomputer of the barcode pasted on the side of reagent vessels in the reagent carrying mechanism 120; the placement varies depending on what kind of reagents a given vessel unit 122 contains. Then, the cap operating mechanism 130 opens the caps of reagent vessels 122a, 122b and 122c in a reagent unit 122 necessary for analysis H. Next, the reagent carrying mechanism 120 spins until the reaction vessel 122a reaches a point just beneath the opening 126d prepared on the lid 124, thereby allowing the stirring mechanism 140 to stir the bead-containing solution in that vessel. After completion of stirring, the reagent carrying mechanism 120 spins further until the reagent vessel 122a reaches a position just beneath the opening 126a prepared on the lid 124, thereby allowing the nozzle tip to aspirate the bead-containing solution therein.

In the meantime, the X-carriage 250 or a moving member in the carrying mechanism 200 has moved to the left uppermost position of the vessel magazine 272a, and holds an unused reaction vessel at that position. Then, the X-carriage 250 moves to the right one among three opposed openings of the delivery station 164 on the buffer plate 160, and puts the reaction vessel on the opening.

The X-carriage 250 starts to pick up a reaction vessel from the left uppermost position of the vessel magazine 272a, then advances in order towards the right in the same row. This first row has 6 reaction vessels. Thus, after 6 reaction vessels have been used up, the X-carriage advances to the second row. After the next 6 reaction vessels have been used up, the X-carriage advances to the third row. When 60 reaction vessels have been used up in this manner, the X-carriage moves to the left uppermost position of the next vessel magazine 272b. When all the reaction vessels in the vessel magazine 272b have been used up, the X-carriage advances to the vessel magazine 272c.

The nozzle holder 104, after having aspirated the beads $B_H$, ascends, moves to a position above the washing basin 150 and stays there for a moment. The washing basin 150 expels cleaning water and washes the outer surface around the nozzle tip, thereby preventing beads adhered to the outer wall of the nozzle tip from contaminating through contact reagents or samples to be aspirated subsequently.

Then, the nozzle holder 104 moves obliquely towards the left until it reaches a position above the opening 126b prepared on the lid 124 of the reagent carrying mechanism 120. The nozzle tip descends until it reaches a reagent vessel 122b placed just below the opening 126b, to draw in by suction a first reagent $R1_H$ in the vessel 122b which is to be used for analysis H. The volume of the reagent $R1_H$ to be extracted is assumed 50 µl here. However, the volume to be extracted may vary depending on the kind of analysis; it may be 20 µl or another. The volume to be extracted can be varied readily by adjustment of the syringe pump 402.

The nozzle holder 104, after aspirating the first reagent $R1_H$, descends again, moves to a position above the washing basin 150, and stays there for a moment. The washing basin 150 expels cleaning water and washes the outer surface of the nozzle holder 104.

After completion of delivery of the reagent R1, the reagent carrying mechanism 120 spins until the reagent unit 122 is put in proper place with respect to the cap operating mechanism 130 which then closes the caps of the reaction vessels 122a and 122b containing beads $B_H$ and the first reagent $R1_H$, respectively.

In the meantime, the X-carriage 250 of the delivering mechanism 200 has moved from the standby position to a position one row below the left uppermost position of the tip magazine 276a, and holds an unused nozzle tip at that position. Then, the X-carriage 250 moves to the left opening of the relay station 164 on the buffer plate 160, and puts the nozzle tip on the opening. Moreover, the X-carriage 250 carries, as appropriate, a nozzle tip to the right opening of the relay station for tip attachment.

The nozzle holder 104 moves obliquely towards the left until it reaches a position above a sample vessel 112 placed on the sample carrying mechanism 110. Sample S1 is placed properly with respect to the nozzle holder 104. The nozzle holder 104 descends until it reaches the sample vessel 112 and aspirates a specific volume of a first sample S1. The volume to be extracted is assumed 50 µl here. However, the volume to be extracted may vary depending on the kind of analysis; it may be 20 µl or another. The volume to be extracted can be varied readily by adjustment of the syringe pump 402. Thus, into the nozzle tip, beads $B_H$, the first reagent $R1_H$, and sample S1 have been collected and stored.

The nozzle holder 104, after having aspirated sample S1, moves until it reaches a position above the right opening prepared on the delivery station 164 of the buffer plate 160. Then, the nozzle holder 104 descends and expels beads $B_H$, the first reagent $R1_H$ and sample stored therein into the reaction vessel positioned there. By this expelling, the first reagent $R1_H$, beads $B_H$ and sample S1 are stirred together for mixture. In the above procedures, the sample is aspirated last. This is to prevent the entry of sample into the reaction vessels 122a and 122b.

The nozzle holder 104, after having expelled its content, moves to a position above the waste outlet 166 on the buffer plate 160, and has the nozzle tip removed from its end by hooking the upper end of the nozzle tip onto a notch of the waste outlet 166. The nozzle tip, thus removed from the end of the nozzle holder 104, is passed through the opening for nozzle tip 292 just below into the waste box 290. Then, the nozzle holder 104 returns to the standby position above the waste basin 150.

Next, the X-carriage 250 of the carrying mechanism 200 moves from the standby position until it reaches a position above the right opening prepared on the delivery station 164 of the buffer plate 160, and picks up the reaction vessel placed at that position. This reaction vessel contains the first reagent $R1_H$, beads $B_H$, and sample S1. The X-carriage 250 moves to the incubator 280, takes the left uppermost position, and descends and holds the reaction vessel in the incubator 280, thereby keeping its content including sample warm at a constant temperature. The temperature of the incubator is assumed 37° C. here.

Normally the time allowed for reaction to proceed in the incubator 280 is about several minutes. It is assumed here that the concentrations of all reagents are so adjusted that the time required for all reactions is the same, such as 9 minutes.

The series of operations as described above complete the first step necessary for analysis H of sample 1. The next step includes addition of a second reagent $R2_H$ to the solution in the reaction vessel here concerned. This operation, however, takes place after completion of the incubation, and during this interlude the system continues other operations necessary for analysis of sample 1.

Next, analysis I of sample 1 will be given as Example 2 illustrating the operation of the whole system. Analysis I has been outlined above; it is distinct in procedure from analysis H. If a given analysis requires the same procedures with analysis H, though reagents to be used are different, the procedures in analysis H of sample 1 are followed.

A nozzle tip has been placed on the left opening prepared on the relay station 162 of the buffer plate 160 as a result of the previous cycle of operation. The nozzle holder 104 moves from the standby position until it reaches a position above the left opening prepared on the relay station 162 of the buffer plate 162. Then, it descends and attaches the nozzle tip to its end. The nozzle holder 104 with the nozzle tip at its end moves obliquely towards the left until it reaches a position above the opening 126b prepared on the lid 124 of the reagent carrying mechanism 120. The nozzle tip descends until it reaches a reaction vessel 122b placed just beneath the opening 126b, and aspirates a first reagent $R1_I$ necessary for analysis I and contained in that reaction vessel. Here the volume of the first reagent $R1_I$ to be aspirated is assumed 50 μl.

Explanation of how the reagent carrying mechanism 120 places a unit of reagents 122 beneath appropriate openings, and how the cap operating mechanism 130 opens/closes the caps of reaction vessels 122a and 122b, is omitted here, but the same operations as were give above for analysis H take place here.

In the meantime, the X-carriage 250 of the carrying mechanism 200 moves to a position one column right of the left uppermost position. The microcomputer incorporated in the system, being well aware that the reaction vessel at the left uppermost position of the vessel magazine 272a has been used already, orders immediately the X-carriage 250 to take the position by one column right from the left uppermost position, and to pick up an unused reaction vessel there. Then, the X-carriage 250 moves to a position above the right opening prepared on the delivery station 164, and places the reaction vessel on that opening.

The nozzle holder 104, after having aspirated the first reagent $R1_I$, moves to a position above the washing basin 150, to have the external wall of the nozzle tip washed there.

In the meantime, the X-carriage 250 of the delivering mechanism 200 has moved from the standby position to the next position for a new nozzle tip of the tip magazine 276a, and holds an unused nozzle tip at that position. Then, the X-carriage 250 moves to the left opening prepared on the relay station 162 of the buffer plate 160, and puts the nozzle tip on that opening.

The nozzle holder 104 moves obliquely towards the left until it reaches a position above sample vessels 122 on the sample carrying mechanism 110. The first step of analysis I does not require beads B. Sample S1 is placed just beneath the nozzle holder 104. Th nozzle holder 104 descends until it reaches a sample vessel 112, and aspirates a specific amount of sample S1 or the first sample. Here the aspirated volume of sample S1 is assumed 50 μl. The nozzle holder 104, after having aspirated sample S1, moves until it reaches a position above the right opening prepared on the delivery station 164 of the buffer plate 160. Then, the nozzle holder 104 descends and expels the first reagent $R1_I$ and sample S1 into the reaction vessel placed there. By this expelling, the first reagent $R1_I$ and the sample S1 are stirred together for mixture. In the above procedures, sample is aspirated last. This is, as outlined above, to prevent the entry of sample into the reaction vessels 122a, 122b and 122c.

Then, the nozzle holder 104 moves to a position above the waste outlet 166 on the buffer plate 160, and has the nozzle tip removed from its end by hooking the upper end of the nozzle tip onto the notch of the waste outlet 166. The nozzle tip is thrown off into the waste box 292. Then, the nozzle holder 104 returns to the standby position.

Next, the X-carriage 250 of the carrying mechanism 200 moves from the standby position until it reaches a position above the right opening prepared on the delivery station 164 of the buffer plate 160, and picks up the reaction vessel placed at that position. This reaction vessel contains the first reagent $R1_H$ and sample S1. The X-carriage 250 moves to the incubator 280, takes a position one column right of the left uppermost position, and descends and keeps the reaction vessel in the incubator 280, such that the solution containing sample in the reaction vessel is kept warm at a constant temperature. The incubation time is the same as above, for example 9 minutes.

A series of operations as described above complete the first step necessary for analysis H of sample 1. The next step includes addition of beads $B_I$ and a second reagent $R2_I$ to the solution in the reaction vessel here concerned. This operation, however, takes place after completion of the incubation, and during this interlude the system continues other operations necessary for analysis of sample 1.

Next, explanation of analysis J of sample 1 will be given as Example 3 illustrating the operation of the whole system. Analysis J has been outlined above; it is distinct in procedure from analyses H and I.

A nozzle tip has been placed on the left opening prepared on the relay station 162 of the buffer plate 160 as a result of the previous cycle of operation. The nozzle holder 104 of the delivering mechanism 100 moves from the standby position above the washing basin 150 until it reaches a position above the left opening prepared on the relay station 162 of the buffer plate 160. Then, the nozzle holder 104 descends and attaches the nozzle tip to its end. The nozzle holder 104 with the nozzle tip at its end moves obliquely towards the left until it reaches a position above the opening 126a prepared on the lid 124 of the reagent carrying mechanism 120. The nozzle tip descends until it reaches a reaction vessel 122a placed just beneath the opening 126a, and aspirates beads $B_J$ necessary for analysis J and kept in that reaction vessel.

Here too, explanation of operation of the reagent carrying mechanism 120, the cap operating mechanism 130 and the stirring mechanism 140 is omitted, but the same operations as were give above take place except that all caps of reaction vessels 122a, 122b and 122c are opened at the same time because in analysis J beads $B_J$, the first reagent $R1_J$ and the second reagent $R2_J$ are aspirated closely in succession by the nozzle tip.

In the meantime, the X-carriage 250 of the delivering mechanism 200 moves to a position two columns right of the left uppermost in the vessel magazine 272a, and holds an unused nozzle tip at that position. Then, the X-carriage 250 moves to a position above the right opening prepared on the delivery station 164, and places the reaction vessel on that opening. The nozzle holder 104, after having aspirated beads $B_J$ and ascended, moves to a position above the washing basin 150, to have the external wall of the nozzle tip washed there with cleaning water.

Furthermore, the nozzle holder 104 moves obliquely towards the left until it reaches a position above the opening 126b on the lid 124. The nozzle holder 104 descends until it reaches a sample vessel 112b, and aspirates the first reagent $R1_J$ necessary for analysis J and kept therein. Here the aspirated volume of the reagent $R1_J$ is assumed 50 $\mu$l. The nozzle holder 104, after having aspirated the first reagent $R1_J$ and ascended, moves to a position above the washing basin 150, to have the external wall of the nozzle tip washed.

In the meantime, the X-carriage 250 of the delivering mechanism 200 moves from the standby position until it reaches an appropriate position above the tip magazine 276a, and holds an unused nozzle tip at that position. Then, the X-carriage 250 moves to a position above the right opening prepared on the delivery station 162, and places the nozzle tip on that opening.

The nozzle holder 104 moves obliquely towards the left until it reaches a position above the opening 126c on the lid 124. The nozzle holder 104 descends until it reaches a reagent vessel 122c just beneath the opening 126c, and aspirates the second reagent $R2_J$ necessary for analysis J and kept therein. Here the aspirated volume of the reagent $R2_J$ is assumed 50 $\mu$l. The nozzle holder 104, after having aspirated the second reagent $R2_J$ and ascended, moves to a position above the washing basin 150, to have the external wall of the nozzle tip washed with cleaning water.

Then, the nozzle holder 104 moves to a position above a sample vessel 112. Below the nozzle holder 104, a sample S1 is placed. The nozzle holder descends, and aspirates a specific amount of sample S1 from the sample vessel 112. Here the volume of sample S1 to be aspirated is assumed 50 $\mu$l.

The nozzle holder 104, after having aspirated necessary reagents and sample, moves until it reaches a position above the right opening prepared on the delivery station 164. Then, the nozzle holder 104 descends and expels its contents into the reaction vessel placed there. Because beads $B_J$, the first and second reagents $R1_J$ and $R2_J$, and sample S1 are expelled at the same time, the first and second reagents $R1_J$ and $R2_J$, beads $B_J$ and sample S1 are stirred together for mixture. Then, the nozzle holder 104 moves to a position above the waste outlet 166, and has the nozzle tip removed from its end. The nozzle tip is thrown off through the opening for nozzle tip 292 into the waste box 290. Then, the nozzle holder 104 returns to the standby position.

Next, the X-carriage 250 of the carrying mechanism 200 moves from the standby position until it reaches a position above the right opening prepared on the delivery station 164, and picks up the reaction vessel placed at that position. This reaction vessel contains the first reagent $R1_J$, the second reagent $R2_J$, beads $B_J$, and sample S1. The X-carriage 250 moves to a position above the incubator 280, and holds the reaction vessel in the incubator 280, such that the solution containing sample in the reaction vessel is kept warm at a constant temperature. The incubation time is 9 minutes, for example.

A series of operations as described above complete the first step necessary for analyses H, I and J of sample 1. Then the next step for analysis H of sample 2 starts. In analysis of J, a subsequent step does not exist but the reaction solution is submitted to measurement immediately after incubation. The measurement takes place following the incubation, and during this interlude the system continues other operations necessary for analysis.

Above explanation has given a complete description of the operations necessary for the first step of analyses H, I and J of sample 1. These operations are substantially the same with analysis H of sample 1 except that in this type of analysis, nozzle tips picked up from the tip magazine 276a and reaction vessels picked up from the vessel magazine 272a have been positioned respectively one column right of the corresponding positions for analysis H. In addition, in this type of analysis, the sample carrying mechanism 110 places a sample vessel 112 containing sample 2 on a position just beneath the nozzle holder 104.

As outlined above, the first step of the analyses here concerned has been completed for the sample of interest. Here it is assumed that the first step of analysis H of sample 1 or Example 1 have ended, and the incubation has been completed. Now explanation will be given of the operations necessary for the second step.

Firstly, it is assumed that the first reagent $R1_H$, beads $B_H$ and sample 1 have been mixed in a first reaction vessel, the mixture has been kept warm at a constant temperature, and incubation has proceeded for a period just in short of the exemplary 9 minutes.

Just at this timing, the nozzle holder 104 of the delivering mechanism 100 moves from the standby position above the washing basin 150 until it reaches a position above the right opening prepared on the relay station 162. Then, the nozzle holder 104 descends and attaches a nozzle tip to its end. The nozzle tip, as described above, has been placed on the right opening on the relay station 162 by the X-carriage 250 of the delivering mechanism 200. The nozzle holder 104 with the nozzle tip moves obliquely towards the left until it reaches a position above the opening 126c prepared on the lid 124. The nozzle tip is lowered, and aspirates the second reagent $R2_H$ necessary for analysis H and kept in a reagent vessel 122c just beneath the opening 126c. Here the volume of the second reagent $R2_H$ to be aspirated is assumed 50 μl.

In the meantime, after the incubation time has passed for the first reaction vessel, the X-carriage 250 moves from the standby position to the left uppermost position of the incubator 280, and holds the first reaction vessel there. Then, the X-carriage places the reaction vessel on the delivery station 164.

The nozzle holder 104, with the nozzle tip retaining the second reagent $R2_H$, moves to a position above the right opening on the delivery station 164. There the nozzle holder 104 descends to allow the nozzle tip to expel the second reagent $R2_H$ into the first reaction vessel placed there that has undergone first incubation. Pressure exerted during expelling promotes mixture by stirring.

The nozzle holder 104 moves to a position above the waste outlet 166 on the buffer plate 160, and has the nozzle tip removed from its end by hooking the upper end of the nozzle tip onto the notch prepared on the waste outlet 166. The nozzle tip is thrown off into the waste box 290. Then, the nozzle holder 104 returns to the standby position.

Next, the X-carriage 250 of the carrying mechanism 200 moves from the standby position to the delivery station 164, and picks up the first reaction vessel placed there. This reaction vessel contains the first reagent $R1_H$, the second reagent $R2_H$, beads $B_H$, and sample S1. The X-carriage 250 moves to a position above the incubator 280, and takes a position one row below the left uppermost. It descends, and keeps the first reaction vessel in the incubator 280, such that the solution containing sample in the reaction vessel is kept warm at 37° C. The incubation time is the same as in the first step, or 9 minutes, for example.

A series of operations as described above complete the second step necessary for analysis H of sample 1. The third step includes measurement of light intensity by the measuring device. This operation, however, takes place after completion of incubation, and during this interlude the system continues other operations necessary for analysis of sample 1.

Next, the second step of analysis I or the latter half of Example 2 will be outlined.

It is assumed here that, according to the above description, the first reagent $R1_I$ and sample 1 have been mixed in the second reaction vessel, the mixture has been kept warm at a constant temperature in the incubator 280, and incubation has proceeded for a period just short of the exemplary 9 minutes.

Just at this timing, the nozzle holder 104 of the delivering mechanism 100 moves from the standby position above the washing basin 150 until it reaches a position above the right opening prepared on the relay station 162. Then, the nozzle holder 104 descends and attaches a nozzle tip to its end. The nozzle tip, as described above, has been placed on the right opening on the relay station 162 by the X-carriage 250 of the delivering mechanism 200. The nozzle holder 104 with the nozzle tip moves obliquely towards the left until it reaches a position above the opening 126a prepared on the lid 124. The nozzle holder descends to allow the nozzle tip to aspirate the beads $B_I$ containing solution necessary for analysis I and kept in the reagent vessel 122a just beneath the opening 126a. Here the volume of the beads $B_I$ containing solution to be aspirated is assumed 50 μl.

In the meantime, after the incubation time has passed for the second reaction vessel, the X-carriage 250 moves from the standby position to a position close to the left uppermost of the incubator 280, and holds a second reaction vessel there. Then, the X-carriage places the reaction vessel on the delivery station 164.

The nozzle holder 104, after having aspirated beads $B_I$ and ascended, moves to a position above the washing basin 150, to have the external wall of the nozzle tip washed with cleaning water.

The nozzle holder 104 moves obliquely towards the left until it reaches a position above the opening 126c prepared on the lid 124. The nozzle tip descends, and aspirates the second reagent $R2_I$ necessary for analysis I and kept in the reagent vessel 122c just beneath the opening 126c. Here the volume of the second reagent $R2_I$ to be aspirated is assumed 50 μl.

The nozzle holder 104, with the nozzle tip retaining the second reagent $R2_I$, moves to a position above the right opening on the delivery station 164. There the nozzle holder 104 descends and allows the nozzle tip to expel beads $B_I$ and the second reagent $R2_I$ into the second reaction vessel placed there that has undergone the first incubation. Pressure exerted during expelling promotes mixture by stirring.

The nozzle holder 104 moves to a position above the waste outlet 166 on the buffer plate 160, and has the nozzle tip removed from its end. The nozzle tip is thrown off into the waste box 290. Then, the nozzle holder 104 returns to the standby position.

Next, the X-carriage 250 of the carrying mechanism 200 moves from the standby position to the delivery station 164, and picks up the second reaction vessel placed there. This reaction vessel contains the first reagent $R1_I$, the second reagent $R2_I$, beads $B_I$, and sample S1. The X-carriage 250 moves to a position above the incubator 280, and takes a position by one row below and by two columns right from the left uppermost. It descends, and keeps the second reaction vessel in the incubator 280, such that the solution containing sample in the reaction vessel is kept warm at 37° C. The incubation time is the same as in the first step or 9 minutes, for example.

A series of operations as described above complete the second step necessary for analysis I of sample 1. The third step includes measurement of light intensity by the measuring device. This operation, however, takes place after completion of the incubation, and during this interlude the system continues other operations necessary for analysis of sample 1.

Next, the second step of Example 3 illustrating the operation of the whole system described above will be outlined.

After the incubation has passed for the third reaction vessel, the X-carriage 250 moves from the standby position to a position close to the left uppermost of the incubator 280, and holds a third reaction vessel there. Then, the X-carriage places the reaction vessel on the shipper station 284.

Subsequently, the nozzle carrier 302 of the shipper mechanism 300 moves towards the left from the standby position above the shipper nozzle washing basin 320 until it reaches a position above the shipper station 284. A shipper nozzle 304 held by the nozzle carrier 302 descends and aspirates the reaction solution in the reaction vessel there. Because the first and second reagents $R1_J$ and $R2_J$, beads $B_J$ and sample S1 total 50 μl each in the reaction vessel, the content in the vessel amounts to 200 μl. The volume to be aspirated by the shipper nozzle 304, however, is assumed 150 μl here. Prior to aspiration of the solution, the shipper nozzle aspirates a minute volume of air into its tube. Following aspiration of the reaction solution, the nozzle carrier 302 raises the shipper nozzle 304 from the shipper station 284, and a second time aspirates a minute volume of air into its tube. By the above operations, the reaction solution 150 μl is sandwiched by layers of air, one from the front and the other from the back. This maneuver ensures the reaction solution to be properly introduced into the flow cell of the measuring device 310.

Subsequently, the shipper nozzle 304 moves to a position above the washing basin for shipper nozzle 320 and stays there, to have the external wall of the shipper nozzle 304 washed with cleaning water. Then, the shipper nozzle is placed just above the opening 330a on the buffer tank 330. At that position, the shipper nozzle 304 descends and aspirates a specific amount of buffer solution. The shipper nozzle 304, after having ascended and aspirated a minute volume of air into its tube, places itself just above the opening 334a of the cleaning water tank 334. There the shipper nozzle 304 descends and aspirates a specific amount of cleaning water. Then, the shipper nozzle 304 moves to a position above the washing basin for shipper nozzle 320 and stays there, to be washed with cleaning water.

From the above operations, within the tube of the shipper nozzle 304 are formed layers of substances consisting of (air), (reaction solution), (air), (buffer solution), (air), and (cleaning water). This collection of layers is moved within the tube by the action of the syringe pump 400, and just at the time when the reaction solution in the collection reaches the flow cell of the measuring device 310, the reaction solution is arrested and subjected to optical measurement. After completion of the measurement, the syringe pump 400 is again put into motion, and buffer solution and cleaning water flow through the flow cell to wash. The fluids, after having passed through the flow cell, are introduced into the waste tank 404.

After completion of the second step of Example 1 and of the second step of Example 2, and passage of exemplary 9 minutes necessary for incubation, the reaction vessel, in the same manner as after the second step of Example 3 described above, is transferred by the X-carriage 250 to the shipper station 284 where the reaction solution therein, then the buffer solution and cleaning water, is aspirated by the shipper nozzle 304. The reaction solution is introduced into the flow cell within the measuring device 310, and subjected to optical measurement, and the residue is disposed of into the waste tank 404.

The above examples are concerned with procedures dealing with sample, the first and second reagents, and beads. Use of this system, however, is not limited to these examples, but can be applied to analysis sparing the use of the second reagent. When analysis spares the use of the second reagent, completion of the first incubation of Example 1 is followed immediately by transference of the reaction vessel to the shipper station 284, to submit the reaction solution therein to optical measurement by the measuring device 310.

Because, in this example, three kinds of reagents are placed as a unit on the reagent carrying mechanism, it is easy to replace reagents as appropriate for each session of analysis. Moreover, 15 units of reagents placed in the reagent carrying mechanism can be easily replaced with another 15 units of reagents necessary for another session of analysis.

In this system delivery of solutions takes place at intersections which the line a nozzle tip moves along makes with the perimeters of three concentric circles. This arrangement, though complicating movement of the reagent carrying mechanism, is helpful for effective delivery of solutions, thereby contributing to compaction of the system. The complicated movement of the reagent carrying mechanism can be satisfactorily made up for by the movement of moving members repeated in cycles until a session of analysis is completed.

The washing basin, also acting as a standby position, is located between the buffer plate and the reagent carrying mechanism. So, when the delivery mechanism is ordered to move, the time required for the nozzle holder to reach a destination can be shortened. Nozzle tips are placed in a tip magazine exclusively used for storage of nozzle tips, being arranged in a matrix pattern, and reaction vessels are placed in a vessel magazine exclusively used for storage of reaction vessels, being arranged in a matrix pattern. These magazines are joined together, placed in a stocker, and supplied as a unit, thereby easing handling of those tips and vessels.

Because the shipper nozzle takes the standby position at the washing basin close to the shipper station, the shipper nozzle can get access to the shipper station quickly, and wash itself while being at standby.

Next, the carrying mechanism of one example in accordance with this invention will be detailed with reference to FIG. 2.

Figure 2:
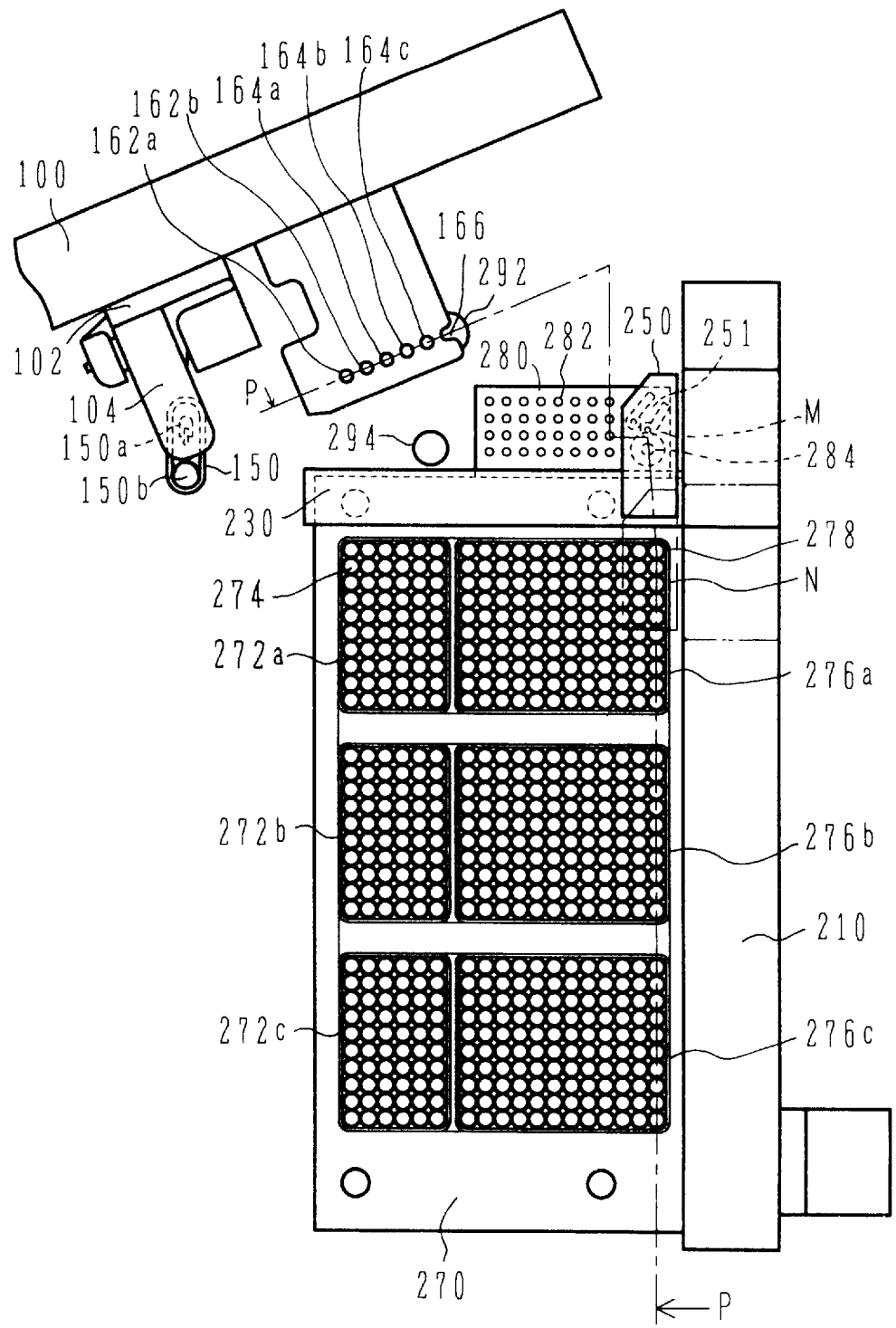
FIG. 2 gives a detailed view of the carrying mechanism and its surrounds as illustrated in FIG. 1.

FIG. 2 gives an enlarged top view of parts of the carrying mechanism and delivering mechanism of all the components illustrated in FIG. 1.

To the delivery mechanism 100 is mounted the nozzle carrier 102 which moves obliquely crosswise in FIG. 1, along a straight course. On the nozzle carrier 102 is placed the nozzle holder 104 which can move up and down along the Z-axis, or an axis normal to the surface of the figure.

The position the nozzle holder takes in FIG. 2 is its standby position. Just beneath the nozzle holder 104 is located the washing basin 150. The washing basin 150 is provided with a washing nozzle 150a and a washing cup 150b. The washing nozzle can eject an amount of cleaning water supplied from the water supply tank 406 illustrated in FIG. 1. When the nozzle holder arrives at this standby position, it receives an amount of cleaning water, to have its external wall washed. Cleaning water to be ejected from the washing nozzle 150a is stored in the washing cup 150b. In this washing cup 150b can be placed the stirring mechanism 140 illustrated in FIG. 1, and by this operation the stirring mechanism 140 can be cleaned. Cleaning water spilt from the washing cup 150b is allowed to flow into the waste tank 404 illustrated in FIG. 1.

At the right end of the delivering mechanism 100 is placed the buffer plate 160. The relay stations 162a and 162b are composed of one opening each, two openings in total. Nozzle tips are carried and placed by the gripping mechanism 251 of the X-carriage 250 onto the relay stations 162a and 162b.

The reason why two openings are prepared on the relay stations 162a and 162b is to meet the requirement of producing reaction in two steps in one cycle. Namely, the relay station has a constitution such that, as described in analysis H, a nozzle tip for the first step can be placed on the relay station 162a and another nozzle tip for the second step can be placed on the relay station 162b. The delivery stations 164a, 164b and 164c have one opening each; three openings in total.

In ordinary analysis, only the right delivery station 164c is used. A reaction vessel is carried and placed by the gripping mechanism 251 of the X-carriage 250 onto the delivery station 164c.

The delivery stations 164a and 164b are used, for example, for diluting sample prior to measurement. This is because, if sample is too concentrated to be measured, it is necessary to dilute it prior to measurement. For sample to be diluted, to each of the delivery stations 164a, 164b and 164c is carried a reaction vessel by the gripping mechanism 251. The nozzle holder 104 expels sample collected from the sample carrying mechanism 110 illustrated in FIG. 1, into a reaction vessel placed on the delivery station 164a. Then, the nozzle holder 104, after having had its end washed, collects a specific amount of diluting solution stored in the sample carrying mechanism 110, and expels it into the reaction vessel on the delivery station 164a. As an example, it is assumed that the injected volume of sample is 20 μl and that of diluting solution 180 μl, and the sample is diluted 10-fold.

If the sample is still too concentrated to be measured even with this dilution, a second dilution should take place. The nozzle holder 104, after having had its end washed, collects a specific amount, say, 20 μl of sample already diluted as above and stored in the reaction vessel on the delivery station 164a, and expels it into a reaction vessel on the delivery station 164b. Then, the nozzle holder 104, after having had its end washed, collects a specific amount, say, 180 μl of diluting solution from the sample carrying mechanism 110, and expels it into the reaction vessel 164b on the delivery station 164b. Through these operations going in succession, the original sample is diluted 100-fold.

As a next step, the nozzle holder, after having washed the nozzle tip in the washing basin 150, collects a specific amount adequate for analysis, say, 50 μl of the diluted sample stored in the reaction vessel on the delivery station 164b, and transfers it to a reaction vessel on the delivery station 164c. Because the delivery station 164c is the site usually used for analysis, the reaction vessel thereupon has received reagents or beads necessary for analysis. Subsequent operations proceed as in ordinary analysis; the gripping mechanism 251 holds the reaction vessel on the delivery station 164c, and carries it to the incubator 280 so that reaction proceeds in that vessel.

Further, when the diluted sample is used for another analysis, sample from the sample carrying mechanism 110 illustrated in FIG. 1 is not poured into the reaction vessel on the delivery station 164c, but instead the sample already diluted and stored in the reaction vessel on the delivery station 164b is poured into the reaction vessel on the delivery station 164c. Subsequent operations may proceed as in ordinary analysis.

The above explanation is concerned with two step dilution for which the delivery stations 164a and 164b are used. When sample is not so high in concentration and well within the range of measurement, one step dilution by the use of delivery station 164a alone will give a satisfactory result. Dilution is not limited to 10-fold but can be varied to any desired magnitude by changing amounts of sample and diluting solution to be mixed.

The carrying mechanism 200 illustrated in FIG. 2 is in a different state from that in FIG. 1. Namely, the X-axis frame 230 that slides along the Y-axis frame 210 of the carrying mechanism 200 is in a position closer to the incubator than that in FIG. 1. This position M is the standby position the X-carriage 250 takes when at rest. While the X-carriage 250 is at position M, the space over the vessel magazines 272a, 272b and 272c, and over the tip magazines 276a, 276b and 276c of the stocker 270, is completely free or devoid of any solid obstacles. Thus, it is possible to replace any one or any combinations of the vessel magazines 276a, 276b and 276c, and the tip magazines 272a, 272b and 272c. When the X-carriage is at position M, the gripping mechanism 251 is positioned at the upper limit point, or the uppermost point along the Z-axis of the X-carriage.

The position along N indicated by an alternating dot- and dash line in FIG. 2 is the standby position the X-carriage takes when in operation. When the X-carriage 250 is at position, the gripping mechanism 251 is at a position N close to the lower limit point, or just above the head of an underlying nozzle tip. During operation, the X-carriage 250, starting from position N, moves to a reaction vessel in the vessel magazine 272a, 272b or 272c, and carries it to the delivery station 164c, or moves to a nozzle tip in the tip magazine 276a, 276b or 276c, and carries it to the relay station 162a. Thus, the X-carriage 250 is used for a number of purposes: It carries a reaction vessel on the delivery station 164c of the buffer plate 160 to an opening prepared on the vessel holder 282 of the incubator 280; it carries a reaction vessel kept in the vessel holder 282 to the shipper station 284; and it carries a reaction vessel on the shipper station 284 to the waste outlet for vessels 294, for disposal.

Figure 3:
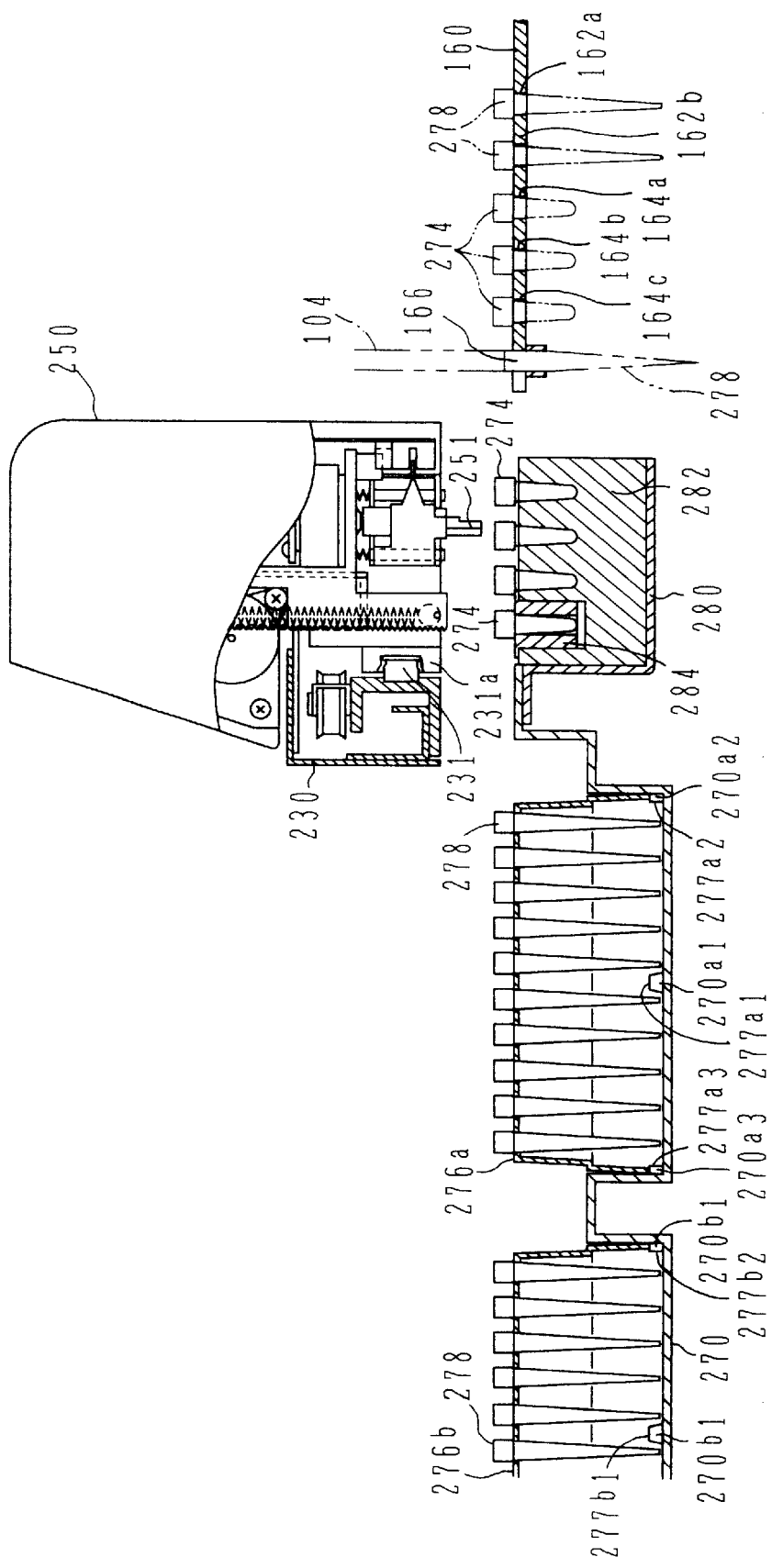
FIG. 3 gives a sectional view along the line P—P in FIG. 2.

Next, the sectional structure of the buffer plate 160, the incubator 280 and the stocker 270 will be outlined with reference to FIG. 3.

FIG. 3 shows a sectional view along the line P—P in FIG. 2, and the left end of the stocker 270 is omitted from the figure.

To the relay stations 162a and 162b on the buffer plate 160 are carried nozzle tips which have been placed in the tip magazine 276a, 276b or 276c by the gripping mechanism 251 of the X-carriage 250. In addition, to the delivery station 164c of the buffer plate 160 is carried a reaction vessel 274 which has been placed in the vessel magazine 272a, 272b or 272c by the gripping mechanism 251.

On the edge of the buffer plate 160 is prepared the waste outlet 166. The nozzle holder 104, as illustrated by an alternating two-dots-and-one-dash line in the figure, has a cylindrical structure, the interior of which is hollow. The nozzle holder 104 fits the outer perimeter of its end to the inner perimeter of the head of a nozzle tip 278; the two elements are jointed together in this operation. For the nozzle tip to be removed at a position above the waste outlet 166, the nozzle holder is transferred to a position above the waste outlet 166, and is elevated, while having its upper end hooked with the notch of the waste outlet 166. By this operation, the nozzle tip 278 is removed from the end of the nozzle holder 104 and recovered in the waste box.

In FIG. 3, to the left of the buffer plate 160 is located the incubator 280. Into the openings of the vessel holder 282 of the incubator 280 are placed reaction vessels 274 containing sample, reagent and/or beads. The vessel holder 282 is a solid block made of aluminum, and on its upper surface are prepared openings fitting to the shape of the reaction vessel. Further, the vessel holder 282 is maintained at 37° C. with a built-in thermocontrol consisting of a heater, and under this condition reaction proceeds in the reaction vessel. To the left of the incubator 280 is located the shipper station 284. The shipper station 284 is formed by fitting a plastic cylinder into the columnar cavity prepared in the substance of the vessel holder 282. The under surface of the plastic cylinder is separated from the bottom of the cavity prepared in the substance of the vessel holder 282.

When the system is at rest, the X-carriage 250 is at the standby position above the incubator 280. To the lowest end of the X-carriage 250 is mounted the gripping mechanism 251. This gripping mechanism 251 can move up and down, but its structure and operation will be detailed below with reference to FIG. 6. The X-carriage 250 can slide in the direction perpendicular to the surface of FIG. 3; an X-axis guide 231a fixed to the X-carriage slides along an X-axis rail 231 fixed to the X-axis frame 230. The structure and operation of those members will be detailed below with reference to FIGS. 5 and 6.

Tip magazines 276a and 276b placed on the stocker 270 are box-shaped containers with no bottom. The tip magazine 276a has a notch 277a1 at the center of its low side edge. The stocker 270 has, at the corresponding position, a projection 270a1 that fits to the notch. The tip magazine 276a has, at the corresponding positions of its other sides, notches such as 277a2, 277a3 and another one not illustrated in the figure that is prepared at the opposite side, and the stocker 270 has projections 270a2 and 270a3, and another one not illustrated here at the corresponding positions. By fitting these four notches to corresponding projections, the tip magazine 276 takes a proper position in the stocker 270.

The tip magazine 276b has four similar notches (only 277b1 and 277b2 are illustrated in the figure), and, by fitting these four notches to the corresponding projections (only 270b1 and 270b2 are illustrated in the figure), takes a proper position in the stocker 270. Further, the tip magazine 276c, and the vessel magazines 272a, 272b and 272c also have similar notches, though not illustrated in the figure, and, by fitting those notches to corresponding projections, take a proper position in the stocker 270.

The system is constructed in profile such that the level of the upper end of nozzle tips 278 on the tip magazines 276a and 276b, the level of the upper end of reaction vessels 274 on the vessel holder 282 of the incubator 280, the level of the upper end of nozzle tips on the relay station 162 of the buffer plate 160, and the level of the upper end of reaction vessels 274 on the delivery station 164 of the buffer plate 160 are all the same. This is because the gripping mechanism 251 of the X-carriage 250 can take the same lowest level in the direction of Z-axis regardless of its position in the system.

Figure 4:
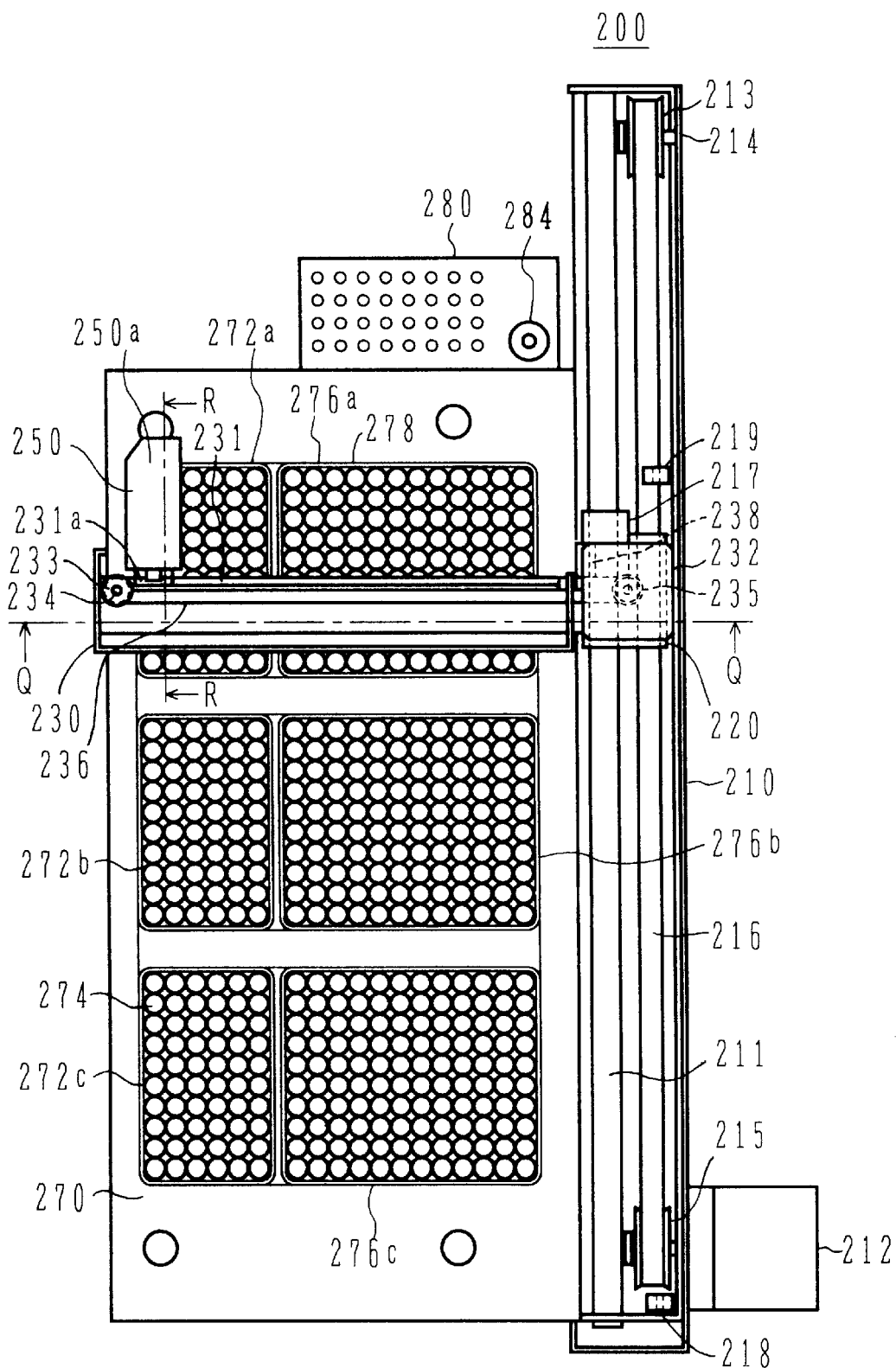
FIG. 4 gives an enlarged top view of the carrying mechanism as illustrated in FIG. 2 with its upper portion removed.

Next, the structure and operation of the carrying mechanism 200 will be outlined with reference to FIG. 4.

FIG. 4 shows an enlarged view of a part of the carrying mechanism 200 in FIG. 2 with special reference to the cross-section of its upper part.

To the Y-axis frame 210 are mounted a Y-guide axis 211, a Y-driving motor 212, and an axle 214 for a Y-coupled pulley 213. To a driving axle of the Y-driving motor 212 is fitted a Y-driving pulley 215. A toothed belt 216 is suspended between the Y-driving pulley 215 and the Y-coupled pulley 213. A part of a Y-carriage 217 which is to slide on the Y-guide 211 is fixed onto the toothed belt 216.

Close to one end of the Y-axis frame 210 is attached a Y-home sensor 218. At the center of the Y-axis frame 210 towards the other end, is attached a reset position sensor 219. Both the Y-home sensor 218 and the reset position sensor 219 consist of photocouplers. Through these photocouplers, a Y-detection plate 220 fixed to a part of the Y-carriage 217 can detect its position, that is, the position of the Y-carriage 217 by, being situated between the two photocouplers, blocking light emitted from light emitting diodes in the photocouplers. The Y-home sensor 218 detects the Y-home position of the Y-carriage 217, while the reset-position sensor 219 detects the Y-reset position of the Y-carriage 217.

Figure 5:
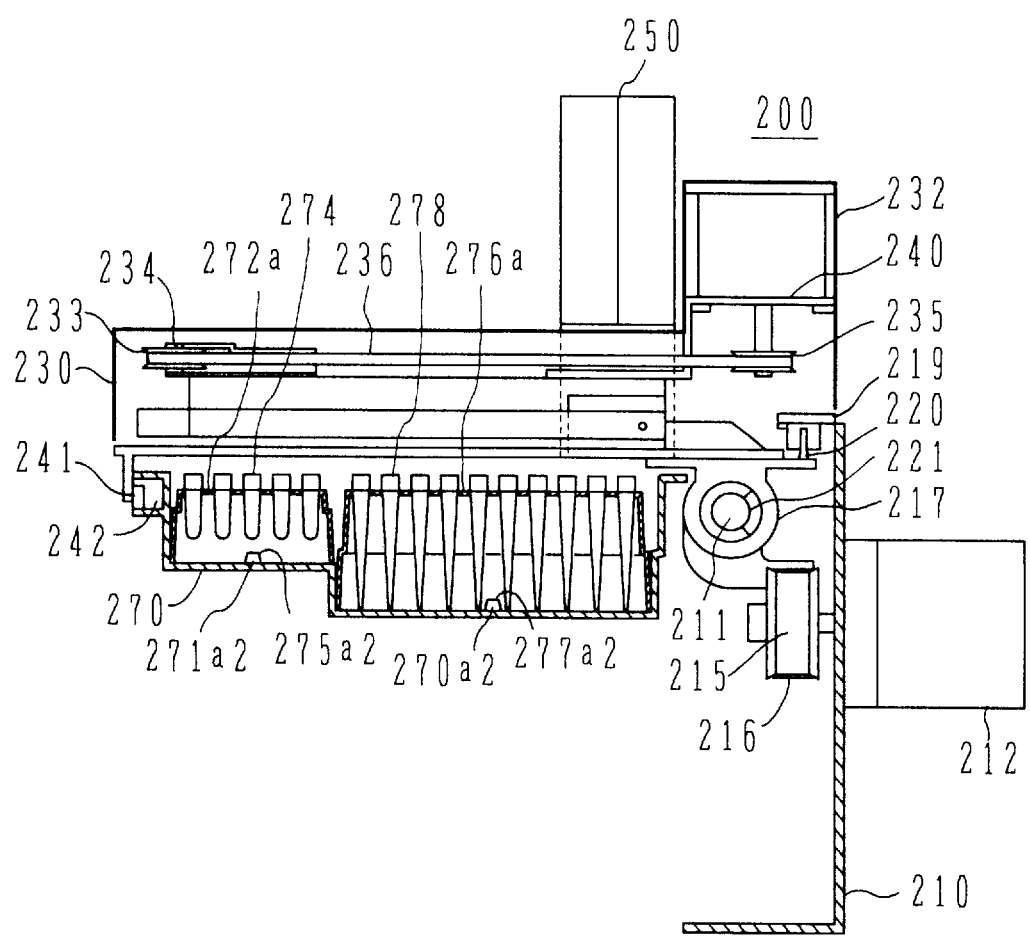
FIG. 5 gives a sectional view along the line Q—Q in FIG. 4.

Between the Y-carriage 217 and the Y-guide axis 211, as illustrated in FIG. 5, is installed a ball push 221, and by this ball push 221 the Y-carriage 217 can slide on the Y-guide axis smoothly.

Based on the above construction the Y-carriage 217 operates as follows. When the Y-driving motor 212 turns round, the spinning force is transmitted through the Y-driving pulley 215 to the toothed belt 216. The Y-carriage 217 fitted to the toothed belt 216 moves in the direction of the Y-axis. In association, the X-axis frame 230 fixed to the Y-carriage 217 moves in the direction of the Y-axis.

To the X-axis frame 230 are mounted an X-rail 231, an X-driving motor 232 and the supporting axle of an X-coupled pulley 233. To the driving axle of the X-driving motor 232 is fitted an X-driving pulley 235. Between the X-driving pulley and the X-coupled pulley is suspended a toothed belt 236. To the X-guide 231a which is to slide on the X-rail 231 is fixed the X-carriage 250. To the toothed belt 236 is joined the X-carriage 250.

Close to one end of the X-axis frame 230 is attached an X-home sensor 238. The X-home sensor 238 is composed of photocouplers. An X-detection plate 220 fixed to a part of the X-carriage 250 can detect its position, that is, the position of the X-carriage 250 by placing itself between the photocouplers, thereby blocking light emitted from light emitting diodes in the photocouplers. The X-home sensor 218 detects the X-home position of the X-carriage 250.

Based on the above construction the X-carriage 250 operates as follows. When the X-driving motor 232 turns round, the spinning force is transmitted through the X-driving pulley 235 to the toothed belt 236. The X-carriage 250 fitted to the toothed belt 236 moves in the direction of the X-axis.

Next, the structure of the carrying mechanism 200 will be outlined with reference to FIG. 5. FIG. 5 shows a sectional view along the line Q—Q in FIG. 4.

To the left end of the X-axis frame 230 is mounted a guide bearing 241 which engages with a guide groove 242 inscribed on the stocker 270. This mechanism restricts the counter clockwise rotation of the Y-carriage 217, and smooths the movement of the Y-carriage 217 by the help of the supportive bearing. To the X-axis frame is connected the X-axis driving motor 232 through a brace plate 240.

The vessel magazine 272a has a notch 275a2 at the center of its low side edge. The stocker 270 has, at the corresponding position, a projection 271a2 that fits to the notch. The vessel magazine 272a has, at the center of its four low side edges, four notches in all. By fitting those notches to corresponding projections, the vessel magazine 272a takes a proper position in the stocker 270.

Figure 6:
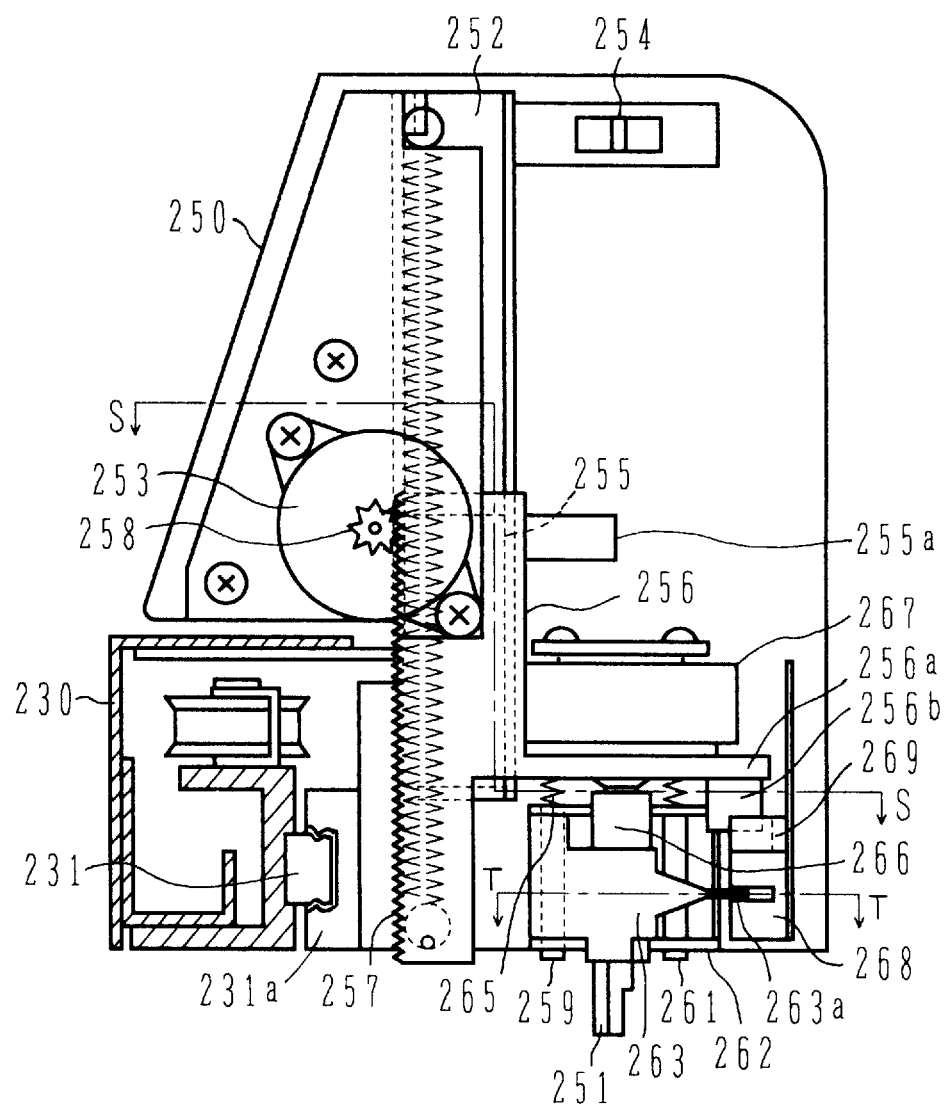
FIG. 6 gives an enlarged sectional view along the line R—R in FIG. 4.

Next, the structure and operation of the X-carriage 250 will be outlined with reference to FIG. 6. FIG. 6 shows an enlarged sectional view along the line R—R in FIG. 4 wherein a cover 250a which covers the right half of the X-carriage is removed for illustration.

To the X-carriage 250 are mounted a linear guide along the X-axis 252, a Z-axis driving motor 253 and a Z-home sensor 254. To a sliding piece 255 which slides on the linear guide along the Z-axis 252 is mounted a Z-carriage 256. To the sliding piece 255 is attached an L-shaped detection piece 255a. The detection piece 255a working on photocouplers consists of a light emitting diode and a photo sensing diode, and the system recognizes that the X-carriage 250 reaches the Z home position when the end of the detection piece 255a crosses the gap between the two diodes. On the left end of the Z-carriage 256 is inscribed a rack 257 which meshes with a pinion 258 joined with the Z-axis driving motor 253.

On the brace plate 256a or a part of the Z-carriage 256 are fixed three guide pins 259, 261 and 260. To the guide pins 259 and 261 is fitted a detector frame 262 in such a manner that the frame can move up and down. To the guide pin 259 is fitted a finger 263 such that the finger can turn round and move up and down freely. Also to the guide pin 260 is attached a finger such that the finger can turn round and move up and down freely (see FIG. 7).

Around the guide pins 259, 260 and 261 is placed a pressing spring 265 in a gap between the brace plate 256*a* and the detector frame 262, and this spring always presses the detector frame 262 downward against the brace plate 256*a*. Accordingly, a pair of fingers 263 fitted to the detector frame 262 is always pressed downward. To the lowest end of the finger 263 is attached the gripping mechanism 251.

On a grip sensor 268 is placed an obstacle sensor 269. The obstacle sensor 269 with photocouplers senses for the presence of any obstacles by checking whether a detection plate 256*b* fixed to the brace plate 256*a* blocks light transmitted in the photocouplers. The obstacle sensor senses the presence of obstacles as follows: When the Z-carriage 256 descends and has the gripping mechanism 251 attached thereto bumped against any obstacle, the gripping mechanism 251 stops moving but the Z-carriage continues to move downward, pressing down on the pressing spring 265, which causes the detection plate 256*b* fixed to the brace plate 256*a* to block light in the photocouplers.

Figure 7:
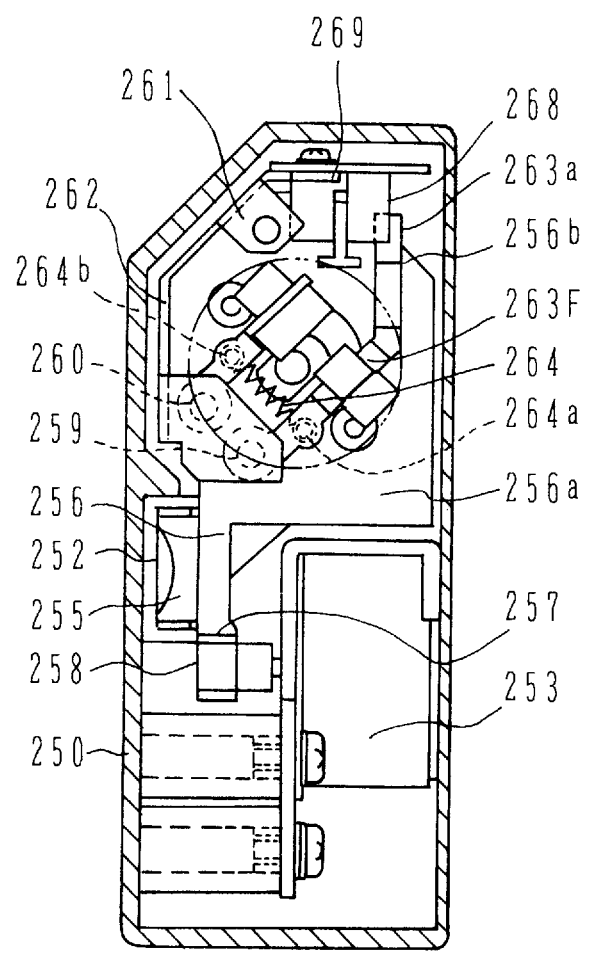
FIG. 7 gives an enlarged sectional view along the line S—S in FIG. 6.
Figure 8:
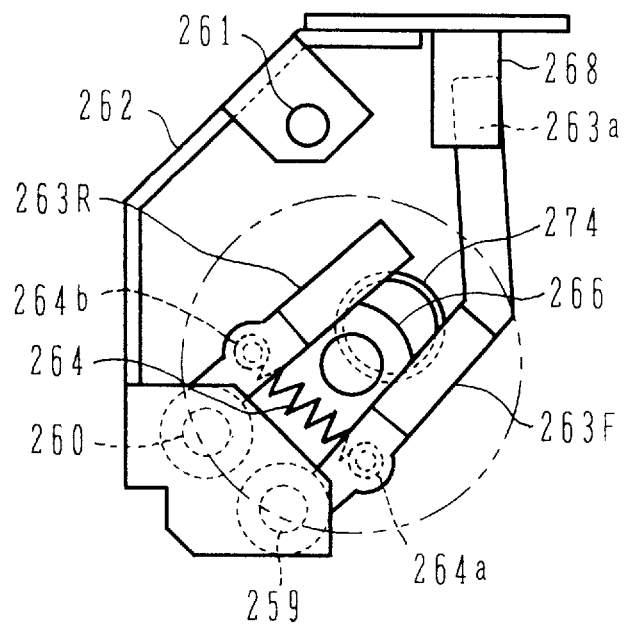
FIGS. 8 and 9 give a side view along the line T—T in FIG. 6, and illustrate how the gripping mechanism closes and opens.
Figure 9:
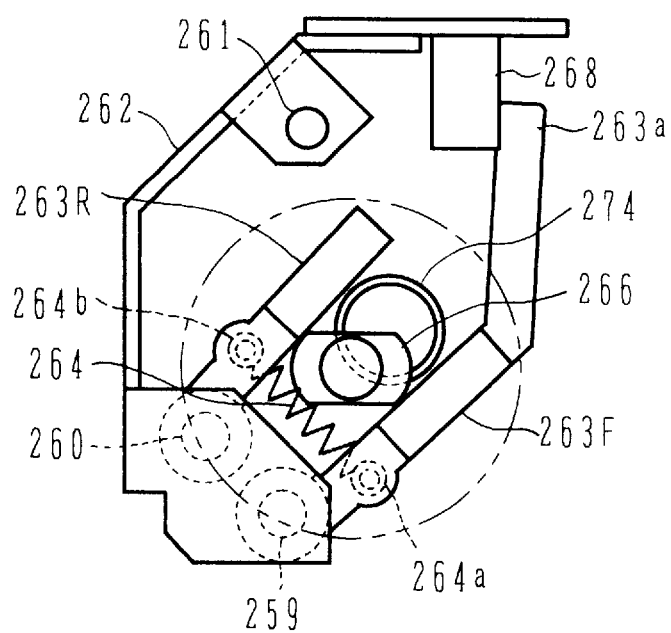

Next, the structure and operation of the finger members will be outlined with reference to FIGS. 7, 8 and 9. FIG. 7 gives an enlarged sectional view along the line S—S in FIG. 6. FIGS. 8 and 9 show a side view along the line T—T in FIG. 6.

To the guide pin 259 fixed to the brace plate 256*a* is fitted a front finger 263F such that the finger can turn round and move up and down freely. Also to the guide pin 260 is fitted a rear finger 263R (FIG. 8) such that the finger can turn round and move up and down freely.

In a gap between the finger 263F and the finger 263R a tensile spring 264 is suspended between pins 264*a* and 264*b*. This spring gives a gripping force to the ends of the two fingers 263F and 263R, when those mechanisms hold a nozzle tip or a reaction vessel. Between the finger 263F and the finger 263R (or pair of finger members) is inserted a cam 266. Accordingly, the inner surfaces of the fingers 263F and 263R make contact with the working surface of the cam 266. The cam 266 is put into rotation by a rotary solenoid. When the cam 266 is put into rotation by the rotary solenoid, the fingers 263F and 263R open/close, thereby opening/closing the gripping mechanism 251.

Opening/closing of the gripping mechanism 251 is detected by the grip sensor 268. The grip sensor 268, being composed of photocouplers, detects opening/closing of the gripping mechanism 251 by checking whether the end 263*a* of the finger 263F blocks light in the photocouplers. When the end 263*a* crosses a gap between the photocouplers, the gripping mechanism is kept closed, and when the end 263*a* is out of the gap between the photocouplers, the gripping mechanism 251 remains open.

FIG. 8 illustrates the fingers 263F and 263R being closed, while FIG. 9 the fingers 263F and 263R being open.

The cross-section of the cam 266, as is obvious from FIG. 9, is composed of two kinds of profile: two arcs with each directing its concave face to each other and two parallel lines between the two arcs. In FIG. 8 the linear parts of the cam 266 are in contact with the respective surface of the fingers 263F and 263R, and the fingers 263F and 263R are kept closed under the pull from the tensile spring 264. Accordingly, the ends of the fingers 263F and 263R can hold the reaction vessel 274. Further, during this operation, the end 263*a* of the finger 263F is inserted into the gap within the grip sensor 268, to block light there, which allows the grip sensor 268 to detect the closure of the gripping mechanism.

When the rotary solenoid 267 is activated further from the state illustrated in FIG. 8, the cam 266 is turned round further. Then, as illustrated in FIG. 9, the fingers 263F and 263R split to open in the face of pull from the tensile spring 264, to open the gripping mechanism 251.

Figure 10:
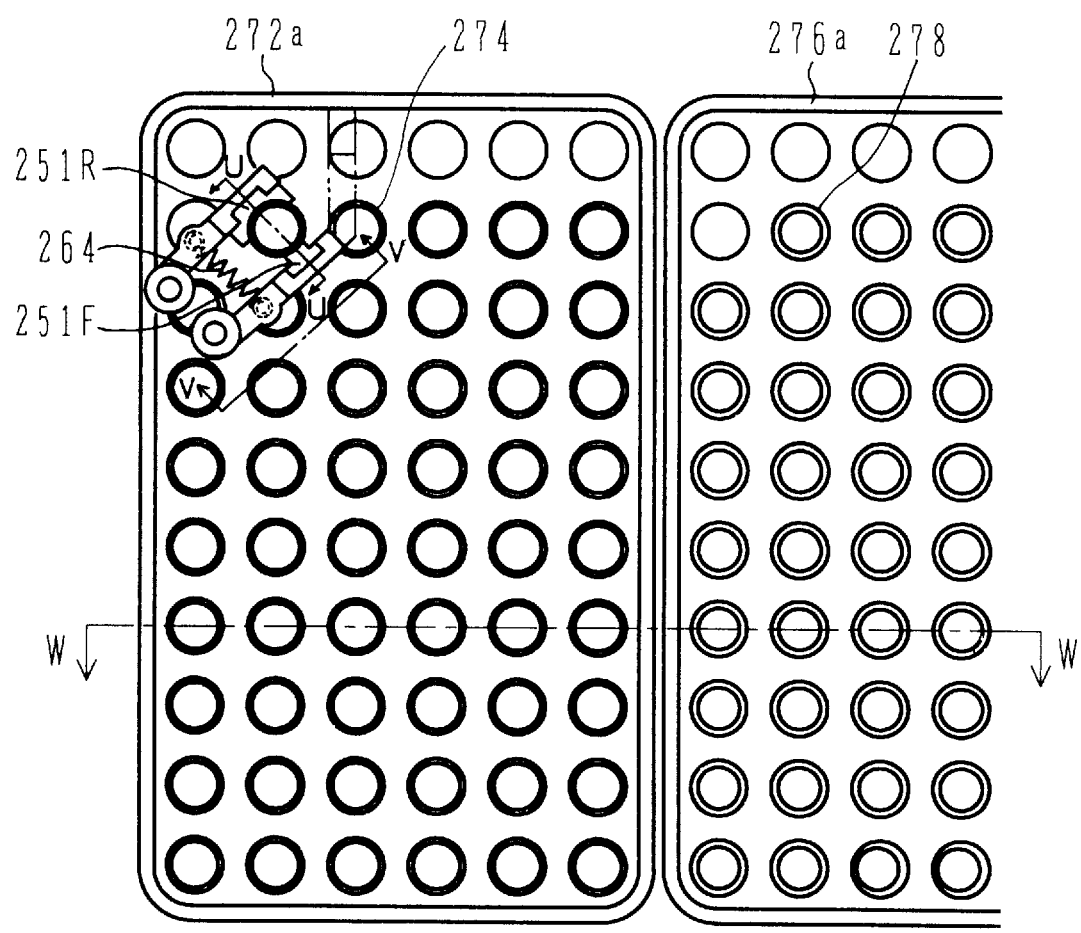
FIG. 10 illustrates how the gripping mechanism grips a reaction vessel on the vessel magazine.

Next, the manner of how the gripping mechanism 251 grips a reaction vessel on a vessel magazine 272*a* will be outlined with reference to FIG. 10.

In FIG. 10, all reaction vessels on the first row of a vessel magazine 272*a* have been used and transferred elsewhere, and of the reaction vessels on the second row, the one on the first column has been used and transferred elsewhere. Thus, the figure illustrates how the gripping mechanism 251 holds, using the front fingertip 251F and the rear fingertip 251R, a reaction vessel on the second column of the second row.

Figure 11:
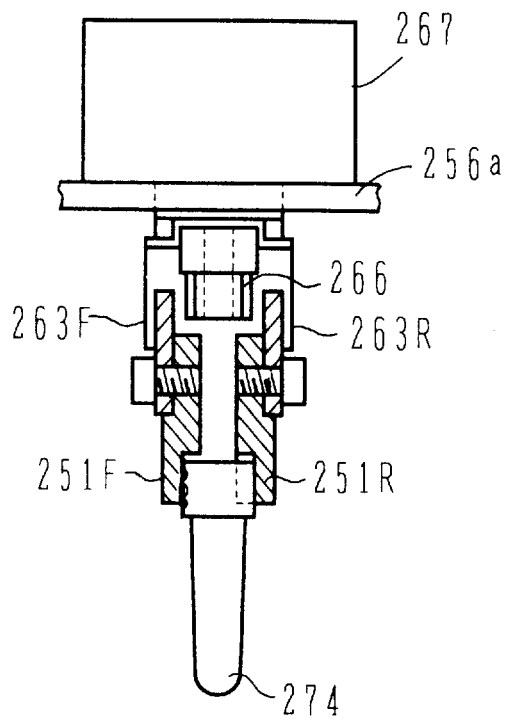
FIG. 11 gives an enlarged side view along the line U—U in FIG. 10.
Figure 12:
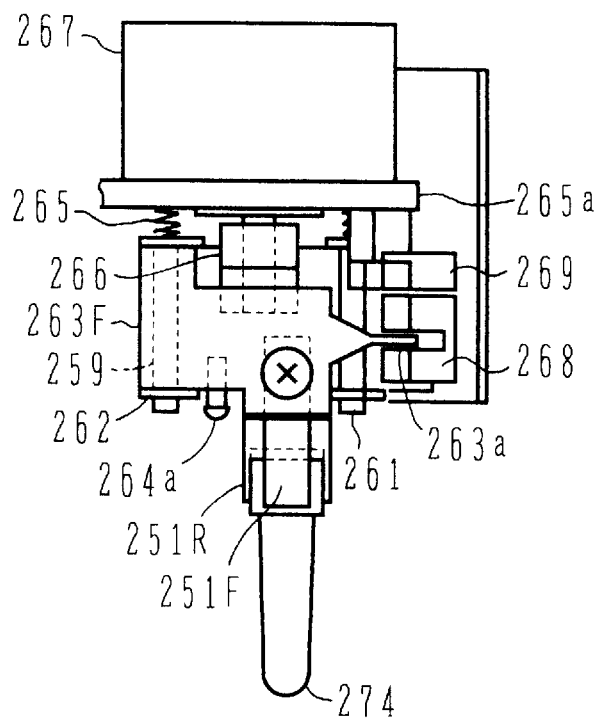
FIG. 12 gives an enlarged side view along the line V—V in FIG. 10.

Next, FIG. 11 shows an enlarged side view along the line U—U in FIG. 10, and FIG. 12 an enlarged side view along the line V—V in FIG. 10. A vessel magazine 272*a* and reaction vessels thereupon are omitted from the figures. Here the numerals are the same in meaning with those in FIG. 6.

As illustrated in FIG. 11, the fingertip 251F of the gripping mechanism 251 is fixed to the finger 263F with a screw, and the fingertip 251R of the gripping mechanism 251 to the finger 263R with another screw. As illustrated in FIGS. 11 and 12, the gripping mechanism 251 holds, using the fingertips 251F and 251R, a reaction vessel 274.

As is evident from FIGS. 10, 11 and 12, the fingertip 251R is larger than the fingertip 251F. This is because the finger 251R enjoys a wider free space to move about because of its relation to the arrangement of vessel magazines to be picked up: as illustrated in FIG. 10, the gripping mechanism is so oriented to a vessel magazine 272*a* that the axis of movement during opening/closing of the fingertips 251F and 251R has an angle of 45° to the row of reaction vessels on the vessel magazine, and, as outlined earlier, the fingertip 251R always enjoys free work space because there is no reaction vessel to be picked up in its upper left quadrant. In other words, the upper left quadrant with respect to a reaction vessel to be picked up is always a free, open space and allows the fingertip 251R to move about freely regardless of the way reaction vessels have been arranged on a vessel magazine 272*a*. Hence, the fingertip 251R is made larger, to ensure the firm grip of reaction vessels. The fingertip 251F, however, is made small because, a number of reaction vessels staying close to it, it must avoid contact with those vessels. The above mode of operation allows the fingertip 251R to be so large as to ensure firm grip of reaction vessels. This contributes to the increased reliability in gripping operation of the gripping mechanism 251. The fact that the fingertip 251F is limited in size because of being inserted between unused reaction vessels, however, does not affect the gripping of the gripping mechanism 251, because the fingertip 251F needs only to act as a support for gripping by holding one side of the reaction vessel.

The above description is concerned with the relation between the fingertips 251F, 251R and the reaction vessels, but it also applies to the relation between the fingertips 251F, and 251R and the nozzle tips.

As described above, when the carrying mechanism 200 picks up nozzle tips on a tip magazine or reaction vessels on a vessel magazine placed on a stocker 270, it starts from an object on the first column of the first row in a matrix, and then moves to another object on the second column of the same row, leaving a free, open space in the upper left quadrant of the object to be picked up. Thus, one fingertip of the gripping mechanism 251 can enjoy a free, wide space regardless of the way the nozzle tips or reaction vessels are arranged on a magazine.

The above mode of operation allows reaction vessels or nozzle tips to be arranged densely on a stocker without impairing the gripping of those reaction vessels or nozzle tips by the carrying mechanism 200, or allows a stocker to be small if the same number of reaction vessels or nozzle tips are to be placed in a stocker. This leads to compaction of the system.

Figure 13:
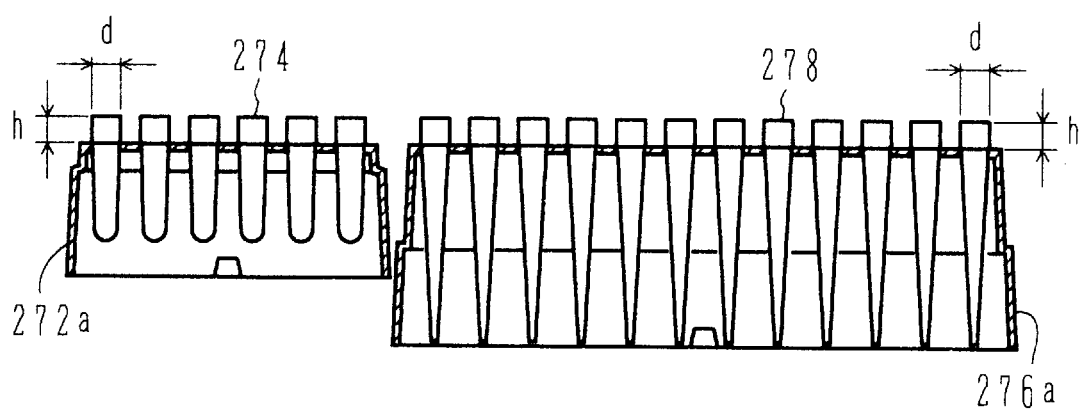
FIG. 13 gives a contracted sectional view along the line W—W in FIG. 10.

Next, the shape of reaction vessels and nozzle tips will be outlined with reference to FIG. 13. FIG. 13 shows a contracted sectional view along the line W—W in FIG. 10.

Reaction vessels 274 are arranged by a unit of 6 on each row of a vessel magazine 272a. Nozzle tips 278 are arranged by a unit of 12 on each row of a tip magazine 276a. A reaction vessel 274 has a length of 25 mm, and a nozzle tip a length of 50 mm. The external diameter of the head of reaction vessels 274 and that of nozzle tips 278 are the same, because the head is the part by which the fingertips 251F and 251R of the gripping mechanism 251 holds the reaction vessel or the nozzle tip. The external diameter d of the head or the upper cylindrical portion of the reaction vessel 274 or the nozzle tip 278 is 7 mm, and the height of the head or the upper portion exposed on the magazine surface is 6 mm.

With this arrangement, one gripping mechanism can handle both the reaction vessel and the nozzle tip. Of course, a greater or lesser difference in the size does not pose a problem in handling, but the same size is desirable for attainment of firm gripping.

Next, the operation of the carrying mechanism 200 will be outlined with reference to FIG. 2 or FIG. 11. The gripping mechanism 251 of the carrying mechanism 200 can be moved back and forth among the various elements in FIG. 2: magazines on a stocker 270, delivery station 162 where nozzle tips are fitted to the nozzle holder, the delivery station 164 where necessary solutions are poured into reaction vessels, the incubator 280, and the waste outlet 294. The movement of the gripping mechanism 251 in this movable area takes place in the directions along the X-, Y- and Z-axes. Accordingly, the carrying mechanism 200 can transfer a reaction vessel 274 or a nozzle tip 278 to any desired place in this movable area.

The X-carriage 250, when the system is at rest, takes position M in FIG. 2 being ready to act. At this position, the Z-carriage 256 is at the home position or the upper limit in the range of the Z-home sensor 254, and the fingers 263F and 263R are above a reaction vessel 274 or a nozzle tip 278 placed on a vessel magazine 272 or a tip magazine 276.

When the system is activated, the X-carriage 250 and the Y-carriage 217 are put into movement by respective driving motors 232 and 212, and are reset to home positions after having passed the detection spots of the home sensors 238 and 218. The Y-carriage 217, after having moved a second time to position M, returns to position N. Position N is the standby position for the gripping mechanism during operation. The X-carriage 250 is reset to its own home position and the Y-carriage 217 is reset to position N through the action of the reset position sensor 219.

When used for analysis, the gripping mechanism 251 moves, starting from position N, to a stocker 270 to seize a nozzle tip or a reaction vessel there, or to the buffer plate 160 or the incubator 280 to seize a reaction vessel there, carries the nozzle tip 278 or the reaction vessel 274 to a desired place, returns to position N, and resets that position. By this operation, the X-Y coordination has the starting point reset, each time the gripping mechanism 251 completes movement, which ensures a proper action of the system.

When the gripping mechanism 251 is placed properly with respect to a nozzle tip 278 or a reaction vessel 274 of interest, the rotary solenoid 267 is excited to spin the cam 266 by 45° counterclockwise, and to open the fingertips 251F and 251R of the gripping mechanism 251, as illustrated in FIGS. 8 and 9. When the Z-carriage 256 is lowered to a specific level by a Z-axis driving motor 253 illustrated in FIG. 6, the gripping mechanism with its fingertips open places properly the fingertips 251F and 251R with respect to a nozzle tip 278 or a reaction vessel 278 so that they may seize the head of the tip or the vessel. Then, when magnetic activation of the rotary solenoid 267 is switched off, the fingertips 251F and 251R of the gripping mechanism 251 seize the nozzle tip 278 or the reaction vessel 274 by its head through the action of the tensile spring 264 suspended between the fingers 263F and 263R. Later, when the Z-carriage returns to home position, the nozzle tip or the reaction vessel is lifted up by the gripping mechanism.

With the gripping mechanism holding the nozzle tip 278 or the reaction vessel 274, the X-carriage 250 and the Y-carriage 217 are moved appropriately to transfer the tip or the nozzle to a desired spot. There the Z-carriage is lowered, the rotary solenoid is activated again to open the fingertips 251F and 251R of the gripping mechanism 251, and the nozzle tip 278 or the reaction vessel 274 is left on the spot. After having put the tip or the vessel in place, the Z-carriage ascends and is reset to home position, the rotary solenoid is switched off, and the X-carriage 250 and Y-carriage 217 return to position N. This completes the carrying operation for a nozzle tip 278 or a reaction vessel 274.

After the gripping mechanism has seized a nozzle tip 278 or a reaction vessel 274, or has released it, the carrying operation is checked on the basis of how light in the grip sensor is interrupted with the tip 263a of the finger 263F.

Next, operation of the obstacle sensor 269 placed on the Z-carriage 256 will be outlined.

When the system is activated for a new analysis, it is generally difficult to reset the system according to the state lastly met in the previous analysis. Or, the state of the system might change during a given analysis: The operator might remove some reaction vessels or replace some vessel magazines or tip magazines with new ones while the system's operation is suspended. Namely, when the system is reset for a new analysis, it is necessary to check for the presence of nozzle tips 278 or reaction vessels 274 on the buffer plate 160, incubator 280 and the shipper station 284, and to remove them, if any.

Thus, prior to analysis, the carrying mechanism 200 moves the gripping mechanism 251 to every spot which can receive reaction vessels 274 or nozzle tips 278, and lowers the Z-carriage 256 with the gripping mechanism kept closed. When there is neither nozzle tip nor reaction vessel, no change takes place in the state of the obstacle sensor 269. If there is a tip or vessel, the tip or the nozzle is recognized as follows: While the gripping mechanism 251 keeps contact with the top of the tip or the vessel here concerned, the Z-carriage continues to move downward in the face of counteraction from the pressing spring 265, which causes the obstacle detection plate 256b to block light between the photocouplers in the obstacle sensor 269.

This operation allows the system to check, prior to analysis, for presence of any nozzle tips or reaction vessels on every station that may act as an obstacle to operation, and to remove those obstacles, if any. If a reaction vessel or a nozzle tip is detected on any one of the stations, the computer acting as the control unit dispatches a command to the carrying mechanism 200 to remove that obstacle. In response to the command, the gripping mechanism 251, reaching a position above the obstacle, ascends for a moment to open the finger members, descends with the finger members kept open, and closes the finger members to seize the obstacle. Then, the gripping mechanism 251 ascends, carries the obstacle to the waste outlet 294, and passes it into the waste box 290.

Further, the system can recognize when a new magazine is set in the stocker 270, and resets a renewed carrying sequence in the following manner: The system checks for the presence of a nozzle tip 278 or a reaction vessel 274 at the first column in the first row on each of tip magazines 276a, 276b and 276c, or on each of vessel magazines 272a, 272b and 272c; when it detects a nozzle tip 278 or a reaction vessel 274 at that position, it resets a renewed carrying sequence; and when it finds no nozzle tip 278 or reaction vessel 274 there, it continues to proceed according to the state lastly met prior to the withdrawal of operation, that is, to seize a nozzle tip 278 or a reaction vessel 274 in the column next to the tip or vessel lastly picked up.

An embodiment of the present invention as described above can achieve highly sensitive measurement in immunoassay by making reaction vessels and nozzle tips disposable, which eliminates the possibility of cross-contamination between samples and reagents.

As the system according to an embodiment of the present invention uses a fixed incubator in which reaction vessels are arranged in a matrix, it is comparatively free from restrictions in reaction time and in repeated injections of samples and reagents as compared with a reaction line in which reaction vessels continue to move in an incubator. Thus, the system of the present invention is sufficiently flexible to meet various types of analysis where, for example, an analysis comprising one step and another comprising two steps are intermingled. In other words, the system of the present invention allows one to make a most adequate combination of steps according to analysis of interest. Accordingly, although the incubation time is fixed in the above examples, it is possible to change the parameters of necessary procedures to adjust the incubation time in accordance with a given analysis.

Further, as the incubator is fixed to the system, it needs only a space sufficiently wide for reaction vessels to be retained securely and to be settled or removed smoothly by a carrying mechanism. Thus, the incubator can be compact, and this, in turn, makes thermostatic control very easy.

The principal carrying mechanism of the present invention consists of three separate components: the delivery mechanism, the carrying mechanism and the shipper mechanism. This constitution allows each mechanism with its own conveying devices to be arranged independently from each other in the system. Thus, the system of the present invention can be more compact in size than the system in which only one carrying mechanism is utilized.

Further, in the system of the present invention, of all the principal carrying mechanisms, it is only the carrying mechanism that moves in a three dimensional space, and its movement consists of displacement along three axes, that is, the X-, Y- and Z-axes normal to each other. This type of movement allows the system to be more compact than the movement of a three dimensional space resulting from a combination of displacement along the Z-axis and rotation around the Z-axis.

Of the above three carrying mechanisms of the system of the present invention, the delivery mechanism and the shipper mechanism are so constructed as to move in a two dimensional space, which allows compaction of the system more readily than the structure which allows three-dimensional movement.

The delivery mechanism and the carrying mechanism are so constructed that they share only the buffer plate in common, and the carrying mechanism and the shipper mechanism are so constructed that they share only the shipper station in common. This construction allows less interference between different carrying mechanisms during operation, thereby enabling those carrying mechanisms to act independently from each other. This increases work efficiency of individual carrying mechanisms, which will lead, as a whole, to the contraction of time necessary for a cycle of operations required for a session of analysis. As a result, this will lead to increased treatment of samples for a unit length of time.

The fingertips of the gripping mechanism are placed with an angle of 45° to the row of reaction vessels, and the upper left quadrant with respect to a reaction vessel to be picked up is always a free space. This allows one finger tip to move about in a wide space regardless of how reaction vessels have been arranged on a vessel magazine. Accordingly, the finger tip in question is made so large as to ensure firm grip. As unused reaction vessels stay under the other fingertip, the fingertip in question is made so small as to avoid contact with those reaction vessels during descending. One fingertip is made so large that it can securely grasp reaction vessels, which contributes to increased reliability of the gripping mechanism. The other fingertip is limited in size because it must avoid contact with reaction vessels during descending. However, its size does not affect the gripping of the gripping mechanism, because it only needs to act as a support during gripping by applying itself to the side of a reaction vessel.

In addition, because the heads of a nozzle tip and a reaction vessel are the same in external diameter and have substantially the same shape, one gripping mechanism can handle both of them. Further, the gripping mechanism of the carrying mechanism is reset to a home position, each time it has completed seizing and carrying a nozzle tip or a reaction vessel. This ensures the accurate action of the gripping mechanism. Furthermore, the obstacle sensor checks for the presence of nozzle tips or reaction vessels on the buffer plate and on the incubator, and automatically disposes of them, if any, with the carrying mechanism. This prevents an incorrect operation due to accidental failures.

Further, the obstacle sensor always checks for the presence of a nozzle tip or a reaction vessel at the first position of a tip magazine or a vessel magazine. This allows the system to recognize quickly at any time whether a new magazine is set or not.

Further, the notches prepared at the edge of a tip magazine or a vessel magazine fit snugly with the projections prepared at the rim of a stocker. This allows the tip magazine or the vessel magazine to take a proper position easily.

Further, the waste outlet for used nozzle tips and reaction vessels is prepared close to the buffer plate or an area common to the moving ranges of the delivery mechanism and the carrying mechanism. This allows the delivery mechanism and the carrying mechanism to take a short course for disposal of used tips and vessels, which results in contraction of time necessary for disposal of waste.

According to the present invention, it is possible to make an assay system compact in size by arranging a vessel magazine, a delivery station and an incubator within the moving range of a gripping mechanism along X- and Y-axes, thereby contracting the range necessary for reaction vessels to take when they are carried. Further, the system of this invention allows the operator to avoid contact with reaction vessels containing samples, by removing automatically any obstacles remaining on a delivery station or on an incubator prior to analysis.

What is claimed is:

1. An analyzing apparatus in which a sample and a reagent react in a reaction vessel to produce a reaction solution, the reaction solution is introduced into a measuring device, and the reaction vessel is discarded, said apparatus comprising:

gripping means capable of seizing a reaction vessel and transporting said reaction vessel to a delivery station;

carrying means for moving said gripping means along X- and Y-axes;

a delivery station;

delivery means for delivering the sample and reagent into said reaction vessel at said delivery station;

an incubator for incubating a mixture of the sample and the reagent in said reaction vessel;

a vessel magazine having a plurality of reaction vessels arranged thereupon; and control means for controlling said carrying means in such a manner as to move said gripping means over said delivery station and over said incubator to check for presence of any obstacle thereon, before said gripping means transfers a reaction vessel from said vessel magazine to said delivery station;

wherein said delivery station, said incubator, and said vessel magazine are disposed in a movable area of said gripping means;

wherein said carrying means is equipped with a moving member having said gripping means, and said moving member is provided with a detecting means for detecting presence of an obstacle; and wherein said gripping means is lowered with finger members kept closed from a position above said delivery station or above said incubator, when said gripping means checks for presence of an obstacle.

2. An analyzing apparatus according to claim 1, wherein, if an obstacle is found on said delivery station or on said incubator as a result of checking for presence of an obstacle, said control means orders said gripping means to seize said obstacle, and then to move said obstacle to a waste position.

3. An analyzing apparatus in which a sample and a reagent react in a reaction vessel to produce a reaction solution, the reaction solution is introduced into a measuring device, and the reaction vessel is discarded, said apparatus comprising:

gripping means capable of seizing a reaction vessel and transporting said reaction vessel to a delivery station;

carrying means for moving said gripping means along X- and Y-axes;

a delivery station;

delivery means for delivering the sample and reagent into said reaction vessel at said delivery station;

an incubator for incubating a mixture of the sample and the reagent in said reaction vessel;

a vessel magazine having a plurality of reaction vessels arranged thereupon;

wherein said vessel magazine holds said reaction vessels in rows; and control means for controlling said carrying means to carry said reaction vessels one by one starting from one end of a topmost row in said vessel magazine to said delivery station;

wherein said delivery station, said incubator, and said vessel magazine are disposed in a movable area of said gripping means; and wherein said gripping means has two finger members of which one is smaller than the other, and of which, when said gripping means seizes a reaction vessel, one finger member is placed on a free, open space devoid of any reaction vessel and the other finger member is placed between adjacent reaction vessels.

4. An analyzing apparatus to claim 3, wherein said carrying means is provided with a detecting means for detecting a reaction vessel, and said control means resets a sequence of how reaction vessels are carried when said detecting means detects a reaction vessel at one end of the topmost row in said vessel magazine.

5. An analyzing apparatus according to claim 3, further comprising a tip magazine containing rows of unused nozzle tips therein, and a tip attaching station for attaching unused nozzle tip to a nozzle holder of said delivery means.

6. An analyzing apparatus according to claim 5, wherein a head of said reaction vessel has substantially the same external diameter as the head of said nozzle tip.

7. An analyzing apparatus according to claim 3, wherein said delivery station has a capacity for plural reaction vessels thereupon, and said delivery means, after having delivered sample and diluting solution into a first reaction vessel at said delivery station, transfers by pipetting a part of a diluted sample thus formed in the first reaction vessel to a second reaction vessel at said delivery station.

8. An analyzing apparatus in which a sample and a reagent react in a reaction vessel to form a reaction solution, the reaction solution is measured in a measuring device, and the reaction vessel is thereafter discarded, said apparatus comprising:

a vessel magazine having a plurality of reaction vessels thereon;

a delivery station for receiving a sample and a reagent into a reaction vessel thereon;

gripping means having finger members for seizing and transferring a reaction vessel;

carrying means for moving said gripping means so as to carry one of said reaction vessels;

control means for controlling movement of said carrying means; and detection means for detecting the existence of a reaction vessel by lowering said gripping means;

wherein said control means controls said carrying means so as to lower said gripping means to permit said detection means to detect a reaction vessel, to be transferred by said gripping means from one of said vessel magazine and said delivery station, from a position above said one of said vessel magazine and said delivery station, before said gripping means transfers said reaction vessel.

9. An analyzing apparatus according to claim 8, wherein said control means comprises judging means for judging the existence of an obstacle by detecting the existence of a reaction vessel at said delivery station.

10. An analyzing apparatus according to claim 9, wherein said carrying means is controlled so as to carry said obstacle from said delivery station to a waste position based on a judgment of said judging means.

11. An analyzing apparatus according to claim 8, wherein said control means comprises recognizing means for recognizing that a vessel magazine is a new vessel magazine by detecting the existence of a reaction vessel at a specific end of a topmost row on said vessel magazine.

12. An analyzing apparatus in which a sample and a reagent react in a reaction vessel to produce a reaction solution, the reaction solution is measured in a measuring device, and the reaction vessel is thereafter discarded, said apparatus comprising:

a tip magazine for holding unused nozzle tips in plural rows, said tip magazine being set at a fixed position;

gripping means having finger members for seizing and transferring a nozzle tip;

a tip attaching station for attaching an unused nozzle tip to a nozzle holder of said delivery means;

carrying means for moving said gripping means so as to carry said unused nozzle tip from said tip magazine to said tip attaching station;

detection means for detecting the existence of a nozzle tip by lowering said gripping means; and control means for controlling said carrying means so as to lower said gripping means to permit said detection means to detect a nozzle tip, to be transferred by said gripping means from one of said tip magazine and said tip attaching station, from a position above said one of said tip magazine and said tip attaching station, before said gripping means transfers said nozzle tip.

13. An analyzing apparatus according to claim 12, wherein said control means comprises judging means for judging the existence of an obstacle by detecting the existence of a nozzle tip at said tip attaching station.

14. An analyzing apparatus according to claim 13, wherein said carrying means is controlled so as to carry said obstacle from said tip attaching station to a waste position based on a judgment of said judging means.

15. An analyzing apparatus according to claim 12, wherein said control means comprises recognizing means for recognizing that a tip magazine is a new tip magazine by detecting the existence of an unused tip nozzle at a specific end of a topmost row on said tip magazine.

* * * * *